US009642780B2

(12) United States Patent
Almhöjd et al.

(10) Patent No.: US 9,642,780 B2
(45) Date of Patent: May 9, 2017

(54) DETECTION AND REMOVAL OF CARIOUS DENTIN TISSUE

(75) Inventors: Ulrica Almhöjd, Bohus-Björkö (SE); Åke Nilsson, Göteborg (SE)

(73) Assignee: RLS Global AB, Göteborg (SE)

(*) Notice: Subject to any disclaimer, the term of this patent is extended or adjusted under 35 U.S.C. 154(b) by 125 days.

(21) Appl. No.: 14/125,714

(22) PCT Filed: Jun. 15, 2012

(86) PCT No.: PCT/EP2012/061494
§ 371 (c)(1),
(2), (4) Date: Feb. 18, 2014

(87) PCT Pub. No.: WO2012/172071
PCT Pub. Date: Dec. 20, 2012

(65) Prior Publication Data
US 2014/0161745 A1    Jun. 12, 2014

Related U.S. Application Data

(60) Provisional application No. 61/497,116, filed on Jun. 15, 2011.

(30) Foreign Application Priority Data

Jun. 15, 2011  (SE) ..................................... 1150542

(51) Int. Cl.
| A61Q 11/00 | (2006.01) |
| A61K 6/00 | (2006.01) |
| A61K 8/41 | (2006.01) |
| A61K 8/20 | (2006.01) |
| A61K 8/22 | (2006.01) |

(52) U.S. Cl.
CPC ............ A61K 6/0047 (2013.01); A61K 6/002 (2013.01); A61K 6/007 (2013.01); A61K 6/0061 (2013.01); A61K 6/0067 (2013.01)

(58) Field of Classification Search
USPC ............. 424/49, 54, 401, 9.7; 433/29, 217.1
See application file for complete search history.

(56) References Cited

U.S. PATENT DOCUMENTS 3,998,945 A * 12/1976 Vit ....................... A61C 17/028
                                                          424/53
2005/0207978 A1   9/2005  Ito et al.
2007/0287122 A1  12/2007  Jensen
2008/0038686 A1   2/2008  Nagai
2010/0159612 A1   6/2010  Ono

FOREIGN PATENT DOCUMENTS

| AU | 2004268546 A1 | 3/2005 |
| AU | 2006208046 A1 | 8/2006 |
| AU | 2010281524 A1 | 2/2012 |
| AU | 2012241705 A1 | 10/2013 |
| CN | 10426448 A | 5/2009 |
| JP | S55-076821 | 6/1980 |
| JP | H10-236914 A | 9/1998 |
| JP | H10-236915 A | 9/1998 |
| JP | 2000-063290 A | 2/2000 |
| JP | 2004/113129 A | 4/2004 |
| JP | 2005-023667 A | 1/2005 |
| JP | 2006-143643 A | 6/2006 |
| JP | 2010-120864 A | 6/2010 |
| SE | 460258 B | 9/1989 |
| WO | WO-98/20838 A1 | 5/1998 |
| WO | WO-99/34765 A1 | 7/1999 |
| WO | WO-00/42974 A1 | 7/2000 |
| WO | WO-00/42975 A1 | 7/2000 |
| WO | WO-02/02061 A2 | 1/2002 |
| WO | WO-02/02063 A2 | 1/2002 |
| WO | WO-02/058692 A2 | 8/2002 |
| WO | WO-2004/032979 A2 | 4/2004 |
| WO | WO 2007/123880 | 11/2007 |
| WO | WO-2007/123880 A2 | 11/2007 |
| WO | WO-2008/048170 A1 | 4/2008 |
| WO | WO-2008/083347 A1 | 7/2008 |
| WO | WO-2008/137444 A1 | 11/2008 |
| WO | WO-2009/096993 A1 | 8/2009 |

(Continued)

OTHER PUBLICATIONS

International-Type Search Report mailed Nov. 28, 2011 for National Application SE 1150542-7 filed Jun. 15, 2011 (Applicants—OraSolv AB) (12 pages).
International Preliminary Report on Patentability completed on Aug. 20, 2013 for Intl. Pat. App. No. PCT/EP2012/061494 filed Jun. 15, 2012 and published as WO 2012/172071 on Dec. 20, 2012. (Applicants—RLS Global AB; Inventors—Almhöjd et al.) (6 pages).
International Search Report mailed on Mar. 13, 2013 for Intl. Pat. App. No. PCT/EP2012/061494 filed Jun. 15, 2012 and published as WO 2012/172071 on Dec. 20, 2012. (Applicants—RLS Global AB; Inventors—Almhöjd et al.) (4 pages).
Written Opinion mailed on Mar. 13, 2013 for Intl. Pat. App. No. PCT/EP2012/061494 filed Jun. 15, 2012 and published as WO 2012/172071 on Dec. 20, 2012. (Applicants—RLS Global AB; Inventors—Almhöjd et al.) (5 pages).

(Continued)

Primary Examiner — Lezah Roberts
(74) Attorney, Agent, or Firm — Ballard Spahr LLP

(57) ABSTRACT

The present invention relates to a kit of parts for detection and removal of carious dentin tissue comprising: (i) one or more compounds being a hydrazine derivative, and (ii) means for chemical treatment of carious dentin tissue. Further, the invention concerns a preparation containing an active, caries-dissolving two-component liquid in the form of a first active, caries-dissolving component and a second component which reduces the aggressiveness of the active component to mucous membranes, a viscosity increasing substance and one or more compounds being a hydrazine derivative. The hydrazine derivative labels carious dentin tissue selectively and substantially irreversibly in the presence of healthy dentin tissue, which is useful in the context of caries removal.

21 Claims, 10 Drawing Sheets

(56) References Cited

FOREIGN PATENT DOCUMENTS

| WO | WO-2010/091280 A1 | 8/2010 |
| WO | WO-2011/014460 A1 | 2/2011 |
| WO | WO-2011/017030 A2 | 2/2011 |
| WO | WO-2012/140272 A1 | 10/2012 |
| WO | WO-2012/172071 A2 | 12/2012 |

OTHER PUBLICATIONS

First Office Action issued Feb. 9, 2015 by the State Intellectual Property Office of China for Application No. 201280029041.2 (Applicant—RLS Global AB) (8 pages).

* cited by examiner

DETECTION AND REMOVAL OF CARIOUS DENTIN TISSUE

CROSS-REFERENCE TO RELATED APPLICATIONS

The present application is a U.S. National Phase Application of International Application No. PCT/EP2012/061494, filed Jun. 15, 2012, which claims priority to Swedish Patent Application No. 1150542-7, filed Jun. 15, 2011; and U.S. Provisional Patent Application No. 61/497,116, filed Jun. 15, 2011, all of which applications are incorporated herein fully by this reference.

TECHNICAL FIELD

The present invention concerns dental caries. In particular, the present invention concerns detection and selective removal of dental caries by chemical treatment when the caries lesions have progressed into the dentin tissue.

BACKGROUND OF THE INVENTION

In the treatment of carious lesions the major part of the carious tissue can be examined by judging the hardness of the affected surface using tactile instruments (so-called probing) and/or by visually observing the well known discoloration known as Maillard products. However, the caries affected surface near the healthy dentin, which is called the transparent zone, is not discoloured.

For early stage caries where the caries only affects the enamel of the tooth different therapies are used. In one therapy one removes the caries affected tissue using mechanical means such as dental drill tools. Another therapy uses a preventive methodology such as fluoridation.

Initial caries, i.e. caries affecting only the enamel of the tooth, is normally detectable for the dentist as a diminished translucence in areas of caries, and can be observed as an opaque area due to the porous enamel. However, detection of caries in the inter proximal area between teeth requires radiographic analysis.

In all situations it might not be possible to remove all carious tissue. For instance, this may be the case when the carious lesions have progressed into the dentin of the tooth. Some carious dentin tissue may then still remain and this carious tissue may become locked in underneath a filling used to repair the tooth. This will certainly cause further development of carious dentin tissue, which can develop unseen due to the fact that it is hidden underneath the filling. When the affected individual becomes aware of the carious dentin tissue it might be hard to save the tooth, and extraction or root filling may be needed.

This problem can of course be handled by excavating more healthy dentin tissue from the tooth; i.e. healthy dentin tissue will be removed in addition to the carious dentin tissue. However, this will lead to a weakening of the tooth strength (i.e. less crystals, hydroxyapatite, and less proteins, respectively), and the crown walls may become too thin. Further this will lead to a decrease in the tooth re-mineralisation process since tissue is replaced by a synthetic material like a composite. Taking away tissue affects the whole tooth, both the inorganic and the organic parts.

US 2007/0287122 describes a method of treating residual caries comprising the steps of a) flushing carious tissue with a stain chosen to readily absorb energy from a chosen laser source, b) allowing some of the stain to be absorbed by the carious tissue; c) rinsing the area, leaving the absorbed stain in the carious tissue; and d) removing carious tissue with ablation by laser of a complimentary wavelength and subsequent etching of remaining inorganic tissue using an acid.

WO 2008/048170 discloses a method for determining the presence of carious dentin tissue by means of infrared spectroscopy, which is based on the finding that ester groups are present in carious tissue in contrast to healthy dentin tissue that lacks ester groups.

WO 98/020838 describes a preparation for chemical-mechanical treatment of carious tissue in the form of a two-component caries-dissolving liquid including a coloring agent such as Erythrosin.

WO 2007/123880 discloses a method and a kit for early stage caries detection wherein the early dental caries may be detected by binding an optically detectable probe such as Hylight Fluor to the enamel caries an using an optical device for detection. Nothing is mentioned about detection of dental caries that has progressed into the dentin tissue; i.e. carious dentin tissue.

It is well known in the art that healthy dentin tissue comprises amide groups. This is described in, for instance, Digestion and Nutrition: In Zoology by Dorit, I L R. and Walker, W. F, Saunders College, page 247 as well as in Primary Structure Determination In Biochemistry by Voet, D. and Voet, G. E., $2^{nd}$ edition, John Wiley & Sons, Inc. NY, at page 156.

Accordingly, there is a need for devices and methods allowing for detection and removal of a maximum of carious dentin tissue without affecting or affecting very little of healthy dentin tissue.

SUMMARY OF THE INVENTION

It is an object of the present invention to overcome or at least mitigate some of the disadvantages associated with the prior art. In particular, it is an object of the invention to provide means for efficient and selective detection and removal of carious dentin tissue.

The present invention is based on the unexpected finding that it is possible to selectively remove carious dentin tissue by chemical means after having visually labelled carious dentin tissue irreversibly and selectively with a compound derived from hydrazine, i.e. a hydrazine derivative, in the presence of healthy dentin.

Surprisingly, the inventors have found that carious dentin tissue labelled with a hydrazine derivative may be removed selectively by chemical means for treatment of carious tissue. Accordingly, when carious dentin tissue was labelled with a hydrazine and subjected to chemical means for treatment of carious dentin tissue all of the carious dentin tissue was removed without affecting the surrounding healthy dentin tissue. In contrast, it was not possible to selectively detect and remove carious dentin tissue using a hydrazine derivative in combination with mechanical means such as a dentist's drill.

In a first aspect the invention relates to a kit of parts for detection and removal of carious dentin tissue comprising: (i) one or more compounds being a hydrazine derivative, and (ii) means for chemical treatment of carious dentin tissue.

In a further aspect the invention relates to a preparation containing an active, caries-dissolving two-component liquid in the form of a first active, caries-dissolving component and a second component which reduces the aggressiveness of the active component to mucous membranes, and a viscosity increasing substance, further comprising one or more compounds being a hydrazine derivative. The preparation may be a liquid, for instance an aqueous composition.

In a further aspect of the invention there is provided a method for labelling and removal of carious dentin tissue using a kit of parts for detection and removal of carious dentin tissue comprising: (i) one or more compounds being a hydrazine derivative, and (ii) means for chemical treatment of carious dentin tissue.

In a further aspect of the invention there is provided a method for labelling and removal of carious dentin tissue using a preparation containing an active, caries-dissolving two-component liquid in the form of a first active, caries-dissolving component and the a second component which reduces the aggressiveness of the active component to mucous membranes, a gel substance and one or more compounds being a hydrazine derivative.

In a further aspect of the invention, there is provided a method for labelling and removal of carious dentin tissue comprising the steps of:
(i) labelling carious dentin tissue by applying one or more compounds being a hydrazine derivative onto one or more tooth comprising carious dentin tissue,
(ii) applying means for chemical treatment of carious dentin tissue to the labelled carious tissue, and
(iii) removal of the labelled carious dentin tissue by mechanical means.

In a further aspect of the invention there is provided a method for labelling and removal of carious dentin tissue comprising the steps of:
(i) labelling carious dentin tissue by applying a preparation containing an active, caries-dissolving two-component liquid in the form of a first active, caries-dissolving component and the a second component which reduces the aggressiveness of the active component to mucous membranes, a gel substance and a compound being one or more hydrazine derivative one or more tooth comprising carious dentin tissue, and
(ii) removal of the labelled carious dentin tissue by mechanical means.

DETAILED DESCRIPTION OF THE INVENTION

Figure 1A:
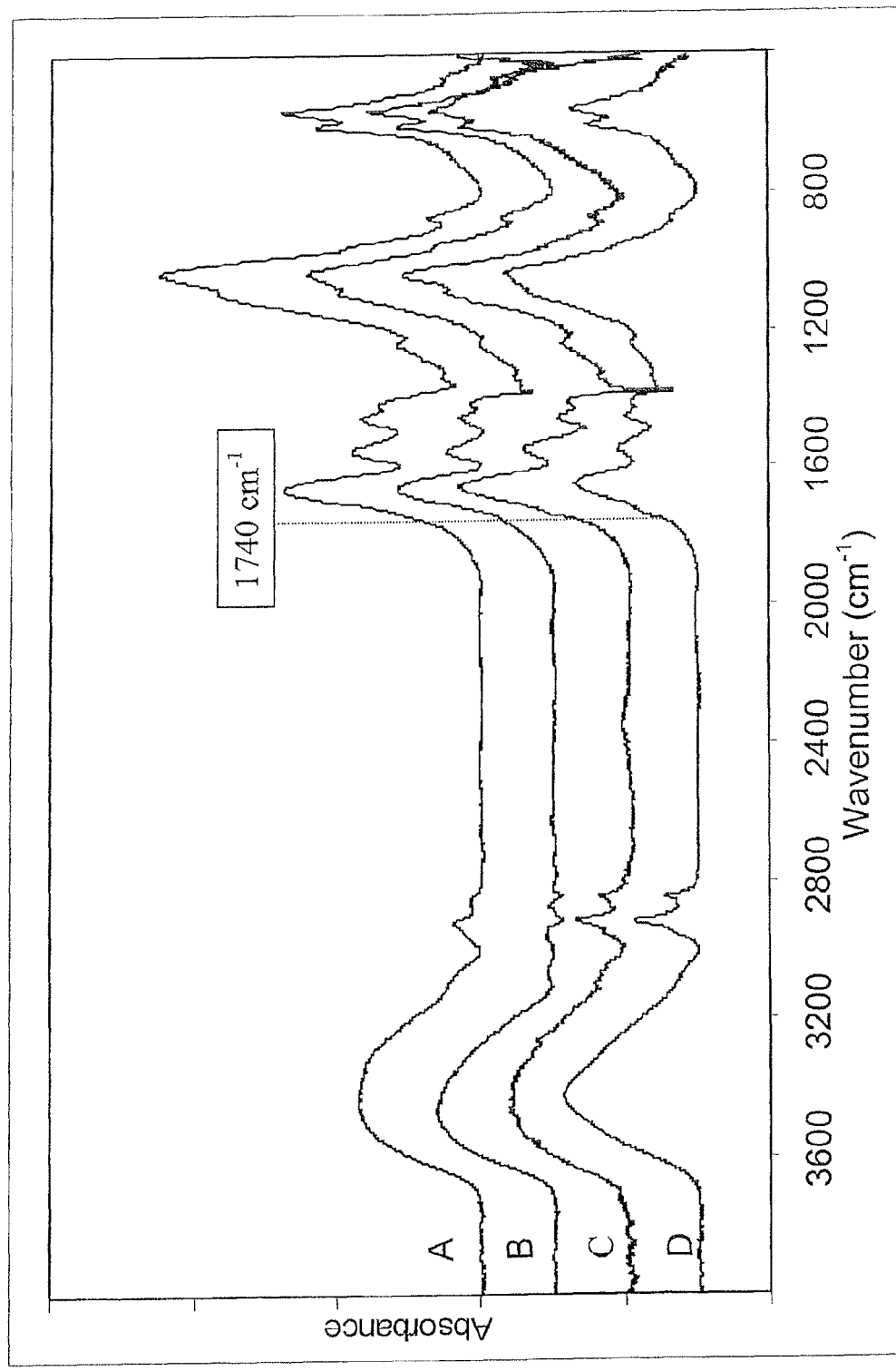
FIG. 1a shows deconvoluted FTIR spectra for healthy dentin tissue (curve A and curve B) collected from two teeth and carious dentine tissue (curve C and curve D) collected from the same two teeth

By selective removal of carious dentin tissue is meant that only carious dentin tissue is removed; i.e. nothing or virtually nothing else is removed. Accordingly, no or very little healthy dentin tissue is removed.

By selective labelling is meant that the labelling takes place only between the carious dentine tissue and the hydrazine derivative without labelling of the healthy dentin tissue.

By irreversible labelling is meant that a hydrazine derivative that has reacted with carious dentine tissue will not be removed during rinsing with for instance water, an aqueous solution of NaCl or an aqueous solution of NaOH.

While not wishing to be bound by any specific theory, it is believed that the irreversible labelling of the carious dentine tissue with a hydrazine derivative is due to the formation of one or more covalent bonds between the carious tissue and the hydrazine derivative.

Since carious dentin tissue contains ester groups and healthy dentin tissue contains amide groups hydrazine derivatives would have been expected to react with the carbonyl groups in both of these, albeit more slowly with the amides. However, the inventors of the present invention observed no reaction whatsoever when a hydrazine derivative was mixed with healthy dentin tissue.

The irreversible labelling of the carious dentin tissue with the hydrazine derivative, possibly through the formation of covalent bonds between carious dentin tissue and the hydrazine derivative, has the advantage that the excess of hydrazine derivative may easily be removed by rinsing without affecting the extent to which the carious dentin tissue is labelled. This allows for more precise caries removal, i.e. removal of as much carious dentin tissue as possible without affecting healthy dentin tissue, since substantially all of the carious dentine tissue will remain labelled after rinsing.

In contrast, a rinsing step in conventional methods using dyes forming non-covalent bonds with carious dentine tissue may easily lead to removal of substantial amounts of dye in addition to the removal of excess of dye resulting in labelling of only a part of the carious dentin tissue. It has been found by the inventors of the present invention that rinsing carious dentin tissue labelled with a dye such as Acid Red forming only electrostatic bonds to the carious dentin tissue results not only in removal of excess dye but also in release of the dye bonded to the carious dentine tissue; i.e. after rinsing only part of the carious dentin tissue is labelled with the dye. Of course, such a partial labelling is not helpful when it is desired to remove all carious dentin tissue.

In the present invention, chemical means are used to remove the carious dentin tissue labelled with the hydrazine derivative. In this document, means for chemical treatment of carious dentin tissue are defined as any preparation or composition that may be used to soften and/or dissolve carious dentine tissue in order to remove it. Such means are well known in the art and will not affect the healthy dentin tissue in a negative way. Thus, healthy dentin tissue surrounding the carious dentin tissue will not have to be protected during removal of carious tissue as required in, for instance, laser based methods.

In a first aspect of the invention there is provided a kit of parts for detection and removal of carious dentin tissue comprising: (i) one or more compounds being a hydrazine derivative, and (ii) means for chemical treatment of carious dentin tissue.

In an embodiment of the invention, there is provided a kit of parts as defined hereinbefore or hereinafter wherein the one or more compounds being a hydrazine derivative is a compound of formula (I)

characterized in that R is a chemical group containing a chromophore or forming a chromophore with $NHNH_2$. The chromophore may be formed before, upon or after reaction of the compound of formula (I) with carious dentine tissue.

In this document, the term "chromophore" means the part of the molecule resulting in its its colour. The colour arises when that part of the molecule absorbs certain wavelengths of visible light and transmits or reflects others.

The hydrazine derivative of formula (I) is, either by itself or after reaction with carious dentin tissue, visible to the naked human eye in daylight, i.e. the hydrazine derivative reflects visible light. In this document, visible light is defined as electromagnetic radiation having a wavelength in the range of about 380 nm to about 750 nm. Therefore, no optical instrument is needed for detection.

It is to be understood that the hydrazine derivative of formula (I) may be, for instance, a carbazide or a hydrazide.

In a further embodiment of the invention there is provided a kit of parts as defined hereinbefore or hereinafter, wherein the one or more compounds being a hydrazine derivative is selected from the group consisting of:

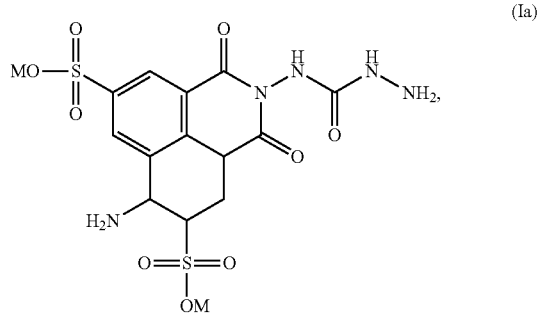

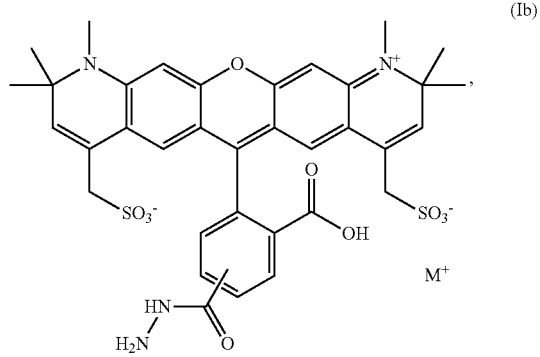

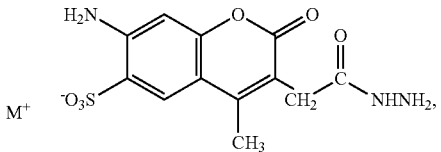

wherein M or $M^+$ represents a monovalent metal ion selected from the group consisting of $Li^+$, $K^+$, and $Na^+$, and

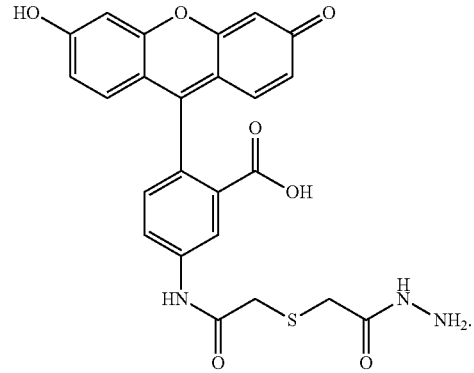

In a further embodiment of the invention, there is provided a kit of parts according to any previous aspect, embodiment or claim wherein the hydrazine derivative is a compound of formula (Ia):

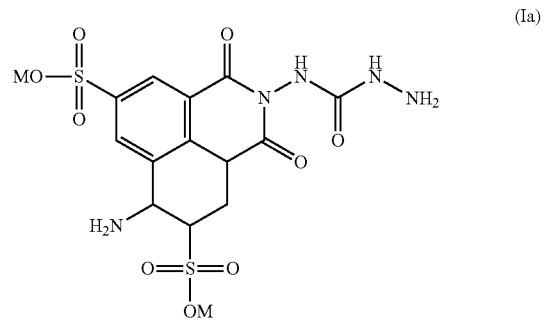

wherein M represents a monovalent metal ion selected from $Li^+$, $K^+$, and $Na^+$. When M is $K^+$ the compound of formula (Ia) is denominated Lucifer Yellow.

In a further embodiment of the invention, there is provided a kit of parts according to any previous aspect, embodiment or claim wherein the hydrazine derivative is a compound of formula (Ib):

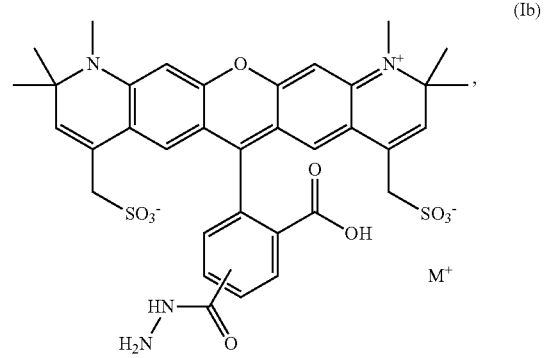

wherein M⁺ represents a monovalent metal ion selected from Li⁺, K⁺ and Na⁺. The trade name of the compound of formula (Ib) when M⁺ is Na⁺ is Alexa Fluor® 594 hydrazide sodium salt.

The chemical name for the compound of formula (Ib) is 6-(2-carboxy-5-(hydrazinecarbonyl)phenyl)-1,2,2,10,10,11-hexamethyl-2,10-dihydro-1H-pyrano[3,2-g]diquinoline-11-ium-4,8-diyl)methanesulfonate.

In a further embodiment of the invention, there is provided a kit of parts according to any previous aspect, embodiment or claim wherein the hydrazine derivative is a compound of formula (Ic):

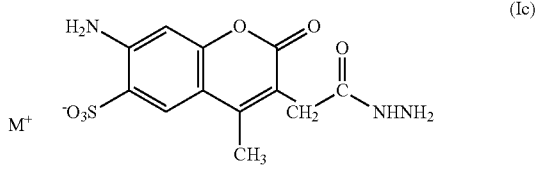

wherein M⁺ represents a monovalent metal ion selected from Li⁺, K⁺ and Na⁺.

The trade name of the compound of formula (Ic) when M⁺ is Na⁺ is Alexa 350.

In a further embodiment of the invention, there is provided a kit of parts according to any previous aspect, embodiment or claim wherein the hydrazine derivative is a compound of formula (Id):

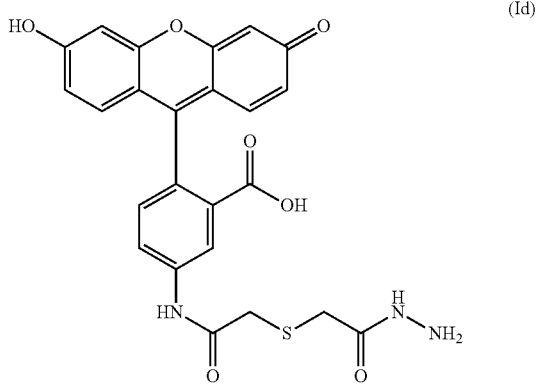 [SMILES: NNC(=O)CSCC(=O)Nc1ccc(-c2c3ccc(=O)cc-3oc3cc(O)ccc23)c(C(=O)O)c1]

The trade name of the compound of formula (Id) is 5-(((2-(carbohydrazino)methyl)thio)acetyl)aminofluorescein, whereas the chemical name suggested by Chemdraw (CS Chemdraw Ultra, Cambridge Soft, USA) for the compound (Id) is 5-(2-2-hydrazinyl-2-oxoethylthio)acetamido)-2-(3-hydroxy-6-oxo-6H-xanthen-9-yl)benzoic acid.

It is to be understood that the hydrazine derivative mentioned hereinbefore or hereinafter may be mixed with one or more other hydrazine derivatives.

Examples of hydrazine derivatives are HiLyte Fluor™ 488 hydrazide, HiLyte Fluor™ 555 hydrazide, HiLyte Fluor™ 594 hydrazide, HiLyte Fluor™ 647 hydrazide, HiLyte Fluor™ 680 hydrazide.

In a further embodiment of the invention, the hydrazine derivative mentioned hereinbefore or hereinafter may be dissolved or dispersed in a solvent such as water, glycerine, propylene glycol, mineral oil, ethanol, acetone, polysorbate, 80, or any like solvent.

In a further embodiment of the invention, the kit of parts mentioned hereinbefore or hereinafter may also comprise a tool for applying the hydrazine derivative to the carious dentin tissue. Examples of such tools include, but are not limited to, a brush, a syringe, a pen, a fibrous pellet or any fibrous web material.

In a further embodiment of the invention, the kit of parts mentioned hereinbefore or hereinafter contains or is used together with a rinsing solution. For instance, the rinsing solution may be water, brine or any physiologically acceptable aqueous solution.

In a further embodiment of the invention, the kit of parts comprises an anesthetic such as lidocaine or benzocaine. The anesthetic may be mixed with the hydrazine derivative or added to the chemical means in the kit of parts.

In a further embodiment of the invention there is provided a kit of parts as defined hereinbefore or hereinafter, wherein said means for chemical treatment of carious dentin tissue is a preparation able to soften and/or dissolve carious dentin tissue.

In a further embodiment of the invention there is provided a kit of parts as defined hereinbefore or hereinafter further comprising means for mechanical removal of the carious dentin tissue that has been softened and/or dissolved by said means for chemical treatment of carious dentin tissue.

In a further embodiment of the invention there is provided a kit of parts as defined hereinbefore or hereinafter, wherein the means for chemical treatment of carious dentin tissue comprises or is a preparation containing an active, caries-dissolving two-component liquid in the form of a first active, caries-dissolving component and a second component which reduces the aggressiveness of the active component to mucous membranes, and a viscosity increasing substance. The preparation may be a liquid preparation, for instance an aqueous composition. The first active, caries-dissolving component may be prepared and kept as a powder, for instance by freeze drying, and subsequently mixed with the second component. The powder may be dissolved in a liquid such as water prior to mixing with the second component.

In a further embodiment of the invention there is provided a kit of parts as defined hereinbefore or hereinafter, wherein the active caries-dissolving component is $Cl^{1+}$, potassium hypochlorite or sodium hypochlorite.

In a further embodiment of the invention there is provided a kit of parts as defined hereinbefore or hereinafter, wherein the component which reduces the aggressiveness of the active component to mucous membranes comprises mixture of amino acids or a mixture of aminoethanediol, 1-amino-3,3-dimethylpropanol and 1,5-diaminopentanol. The amino acids may be deprotonated or exist in zwitterionic form.

In a further embodiment of the invention there is provided a kit of parts as defined hereinbefore or hereinafter, wherein the amino acids are three amino acids with different charge states: one neutral, one with a negative net charge and one with a positive net charge.

In a further embodiment of the invention there is provided a kit of parts as defined hereinbefore or hereinafter, wherein the viscosity increasing substance is a gel.

In a further embodiment of the invention there is provided a kit of parts as defined hereinbefore or hereinafter, wherein the gel is carboxymethyl cellulose or a polysaccharide substance.

The gel substance mentioned hereinbefore or hereinafter adds viscosity to the two-component liquid and should have such properties that the aggressive influence of the active caries-dissolving component to mucous membranes is reduced.

In a further embodiment of the invention there is provided a preparation as defined hereinbefore or hereinafter, further comprising one or more compounds being a hydrazine derivative. The preparation may be a liquid preparation such as an aqueous composition. The one or more compounds being a hydrazine derivative is as defined hereinbefore or hereinafter.

In a further embodiment of the invention there is provided a preparation as defined hereinbefore or hereinafter, wherein the caries-dissolving component is aqueous NaOCl in a concentration of <1% (w/w) and the component which reduces the aggressiveness of the active component to mucous membranes comprises glutamic acid, leucine, lysine, NaCl, a gel substance which is high viscosity carboxymethylcellulose, and one or more compounds being a hydrazine derivative. The preparation may be a liquid preparation such as an aqueous composition. The one or more compounds being a hydrazine derivative is as defined hereinbefore or hereinafter. Additionally, the preparation may comprise $TiO_2$.

In a further embodiment of the invention, there is provided a kit of parts or a preparation as mentioned hereinbefore or hereinafter, further comprising a dye. Examples of dyes include, but are not limited to, Erythrosin (E 127 B) and hydrazine derivatives.

In a further embodiment of the invention, there is provided a kit of parts as mentioned hereinbefore or hereinafter wherein the means for chemical treatment of carious tissue is the preparation Carisolv®. The preparation Carisolv® is an aqueous composition comprising a first active component NaOCl in a concentration of 1-2% (w/w), a second component having a pH between 9.5 and 10.5 and comprising a mixture of glutamic acid, leucine and lysine 0.5-1.5% (w/w), NaCl 0.5% (w/w), and high viscosity carboxymethyl cellulose gel 2.5-5% (w/w). The composition may further comprise $Na_2$-Erythrocine (coloring agent).

In a further aspect of the invention, there is provided a kit of parts as mentioned hereinbefore or hereinafter wherein the chemical means for removal of carious tissue is the preparation PerioPlus®. The preparation PerioPlus® is an aqueous composition comprising a first active component NaOCl in a concentration of 1-2% (w/w), a second component having a pH between 9.5 and 10.5 and comprising a mixture of glutamic acid, leucine and lysine 0.5-1.5% (w/w), NaCl 0.5% (w/w), TiO2 0.03% (w/w) and medium viscosity carboxymethyl cellulose gel 2.5-5% (w/w).

In a further embodiment of the invention there is provided a kit of parts as mentioned hereinbefore or hereinafter wherein the means for chemical treatment of carious dentin tissue is the preparation Carisolv® where the coloring agent has been replaced with a hydrazine derivative of formula (I) such as Lucifer Yellow. Thus, the means for chemical treatment of carious tissue may be a preparation that is an aqueous composition comprising a first active component NaOCl in a concentration of (1-2% (w/w), a second component having a pH equal to or less than 10 and comprising a mixture of glutamic acid, leucine and lysine 0.2-0.4 w/w), NaCl (0.3 w/w), and high viscosity carboxymethyl cellulose gel (3 w/w). The composition may further comprise $Na_2$-Erythrocine (coloring agent). High viscosity of carboxymethyl cellulose is defined as 1500-3000 centi poise (cP) in 1% $H_2O$ (25° C.).

In a further embodiment of the invention, there is provided the use of a kit of parts as mentioned hereinbefore or hereinafter for selective detection and treatment of root caries.

In a further embodiment of the invention, there is provided the use of a kit of parts as mentioned hereinbefore or hereinafter for selective detection and treatment of caries in a root canal of a tooth.

In a further embodiment of the invention, there is provided the use of a preparation as mentioned hereinbefore or hereinafter for selective detection and treatment of root caries.

In a further embodiment of the invention, there is provided the use of a preparation as mentioned hereinbefore or hereinafter for selective detection and treatment of root caries.

In a further embodiment of the invention, there is provided a preparation for chemical treatment of caries containing an active, caries-dissolving two-component liquid in the form of a first active, caries-dissolving component and the a second component which reduces the aggressiveness of the active component to mucous membranes, a gel substance and a compound being one or more hydrazine derivative. The hydrazine derivative may be a hydrazine derivative of formula (I) as defined hereinbefore or hereinafter. In one embodiment, the hydrazine derivative is Lucifer Yellow. The caries-dissolving component may be $Cl^{1+}$, potassium hypochlorite or sodium hypochlorite. The component which reduces the aggressiveness of the active component to mucous membranes may be a mixture of amino acids or a mixture of aminoethanediol, 1-amino-3,3-dimethylpropanol and 1,5-diaminopentanol. The component which reduces the aggressiveness of the active component to mucous membranes may comprise three amino acids with different charge states: one neutral, one with a negative net charge and one with a positive net charge. The gel substance may be a carboxymethyl cellulose or a polysaccharide substance. The carboxymethyl cellulose may be high viscosity carboxymethyl cellulose.

In a further embodiment of the invention there is provided a preparation being an aqueous composition comprising a first active component NaOCl in a concentration of 1-2% (w/w), a second component having a pH equal to or less than 10 and comprising a mixture of glutamic acid, leucine and lysine 0.2-0.4 w/w), NaCl 0.3 (w/w), $Na_2$-Erythrocine (coloring agent) in high viscosity carboxymethyl cellulose gel (3 w/w), and Lucifer Yellow. The preparation may further comprise $TiO_2$, for instance in a concentration of 0.03% (w/w). The concentration of Lucifer Yellow may be between 15 and 50 mM.

In a further aspect of the invention there is provided a method for labelling and removal of carious dentin tissue using a kit of parts for detection and removal of carious dentin tissue comprising: (i) one or more compounds being a hydrazine derivative, and (ii) means for chemical treatment of carious dentin tissue. The one or more hydrazine derivative may be a compound of formula (I) as defined hereinbefore or hereinbelow.

In a further aspect of the invention there is provided a method for labelling and removal of carious dentin tissue using a preparation containing an active, caries-dissolving two-component liquid in the form of a first active, caries-dissolving component and the a second component which reduces the aggressiveness of the active component to mucous membranes, a gel substance and one or more compounds being a hydrazine derivative. The hydrazine derivative may be a hydrazine derivative of formula (I) as defined hereinbefore or hereinbelow. In one embodiment, the hydrazine derivative is Lucifer Yellow. The caries-dissolving component may be $Cl^{1+}$, potassium hypochlorite or sodium hypochlorite. The component which reduces the aggressiveness of the active component to mucous membranes may be a mixture of amino acids or a mixture of aminoethanediol, 1-amino-3,3-dimethylpropanol and 1,5-diaminopentanol. The component which reduces the aggressiveness of the active component to mucous membranes may comprise three amino acids with different charge states: one neutral, one with a negative net charge and one with a positive net charge. The gel substance may be a carboxymethyl cellulose or a polysaccharide substance. The carboxymethyl cellulose may be high viscosity carboxymethyl cellulose.

In a further aspect of the invention, there is provided a method for labelling and removal of carious dentin tissue comprising the steps of:
(i) labelling carious dentin tissue by applying one or more compounds being a hydrazine derivative onto one or more tooth comprising carious dentin tissue,
(ii) applying means for chemical treatment of carious dentin tissue to the labelled carious tissue, and
(iii) removal of the labelled carious dentin tissue by mechanical means.

In a further aspect of the invention there is provided a method for labelling and removal of carious dentin tissue comprising the steps of:
(i) labelling carious dentin tissue by applying a preparation containing an active, caries-dissolving two-component liquid in the form of a first active, caries-dissolving component and the a second component which reduces the aggressiveness of the active component to mucous membranes, a gel substance and a compound being one or more hydrazine derivative one or more tooth comprising carious dentin tissue, and
(ii) removal of the labelled carious dentin tissue by mechanical means.

In a further aspect of the invention, there is provided a method for labelling and treatment of root caries comprising the steps of:
(i) labelling carious tissue by applying one or more compounds being a hydrazine derivative onto the surface affected by caries,
(ii) applying means for chemical treatment to the labelled carious tissue, and
(iii) removal of the labelled carious dentin tissue by mechanical means.

In a further aspect of the invention there is provided a method for labelling and treatment of root caries comprising the steps of:
(i) labelling carious dentin tissue by applying a preparation containing an active, caries-dissolving two-component liquid in the form of a first active, caries-dissolving component and the a second component which reduces the aggressiveness of the active component to mucous membranes, a gel substance and a compound being one or more hydrazine derivative one or more tooth comprising carious dentin tissue, and
(ii) removal of the labelled carious dentin tissue by mechanical means.

In a further aspect of the invention, there is provided a method for labelling and treatment of the root canal of a tooth comprising the steps of:
(i) labelling carious tissue by applying one or more compounds being a hydrazine derivative in the root canal of a tooth,
(ii) applying means for chemical treatment of carious tissue to the labelled carious tissue, and
(iii) removal of the labelled carious dentin tissue by mechanical means.

In a further aspect of the invention there is provided a method for labelling and treatment of the root canal of a tooth comprising the steps of:
(i) labelling carious tissue by applying a preparation containing an active, caries-dissolving two-component liquid in the form of a first active, caries-dissolving component and the a second component which reduces the aggressiveness of the active component to mucous membranes, a gel substance and a compound being one or more hydrazine derivative one or more tooth comprising carious dentin tissue, and
(iii) removal of the labelled carious tissue by mechanical means.

In a further embodiment of the invention, there is provided a method as described hereinbefore or hereinafter further comprising rinsing steps, for instance after step (i), step (ii) and/or step (iii).

In a further embodiment of the invention, there is provided a method as described hereinbefore or hereinafter wherein the means for mechanical removal of the labelled carious dentin tissue is a scraping instrument.

In a further embodiment of the invention, there is provided a method as described hereinbefore or hereinafter wherein the one or more hydrazine derivative is as described hereinbefore or hereinafter.

In a further embodiment there is provided a method for labelling and removal of carious dentin tissue comprising labelling carious tissue, possibly in the presence of healthy dentin, with a hydrazine derivative as defined hereinbefore or hereinafter. For instance, the hydrazine derivative may be a compound of formula (I) as defined hereinbefore or hereinbelow. The method may further comprise a rinsing step. Further, the method may comprise treatment of the labelled carious tissue with chemical means for treatment of carious dentin tissue as defined hereinbefore or hereinafter. For instance, the chemical means may be the preparation Carisolv®.

In a further embodiment of the invention there is provided a method for labelling and removal of carious dentin tissue using a kit of parts or a preparation as described hereinbefore or hereinafter.

It is to be understood that the method as described hereinbefore or hereinafter may be used repeatedly.

The invention is illustrated, but not limited, by the following Examples.

EXAMPLES

Chemicals used in following examples were purchased from Ultradent, Sigma, Aldrich and Invitrogen, respectively.

SEEK was purchased from Ultradent Products (USA), Lucifer Yellow, i.e. compound Ia above where M is K$^+$ was purchased from Sigma. Acid red 1 was purchased from Aldrich. Alexa Fluor®594 sodium salt, Alexa 350 and 5-(((2-(carbohydrazino)methyl)thio)acetyl)aminofluorescein were purchased from Invitrogen.

The chemical structure for Acid red 1 is indicated below.

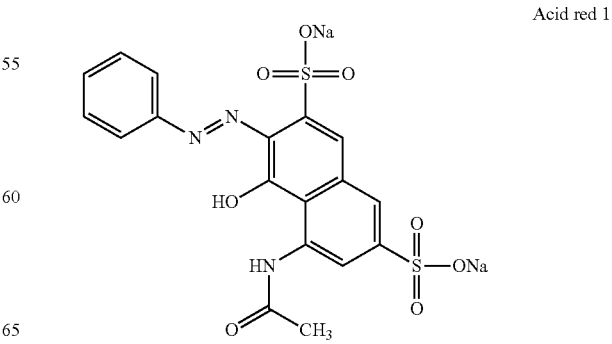

Acid red 1

ABBREVIATIONS

FTIR Fourier Transform Infrared Spectroscopy
TOF SIMS Time-of-flight secondary ionization mass spectrometry
FT Fourier transform
IR Infrared Spectroscopy
u mass/charge
s second
nm nanometer
KeV Kilo electron Voltage
pA pico Ampere
amu atomic mass unite
MQ Utra pure water, from Milli-Q-systems, Milli Pore (USA)
cP Centipoise
w/w weight of solute per weight of solution
M mol/liter
mM mmol/liter

Example 1

Two extracted permanent human teeth with no previous dental restorations were selected due to their severe carious tissue status and analysed with FTIR within one week after extraction. The outermost part of the carious dental lesions was removed. The remaining dental carious tissue was divided into two layers; one outer layer with discoloured, soft and infected dental carious tissue and one inner layer that was seen as uncoloured and excavated down to the estimated hardness of the remaining healthy dentin by tactile procedures. For each tooth, one sample was taken from healthy dentin and another sample was taken from the inner layer of carious tissue. After incubation in purified water they were left to dry at ambient temperature. The dry weight of each tooth sample was approximately 1 mg. Each sample was then mixed with potassium bromide (KBr) before subsequent FTIR examination with a total pellet weight of 100 mg. The IR analyses were performed using a Mattson Cygnus 100 FTIR spectrophotometer with 4 $cm^{-1}$ resolution. The instrument was purged with analytical instrument quality air to remove atmospheric $CO_2$ and $H_2O$, dried and purified with a Balstron type 75-60 conditioner. The spectra were baseline corrected using the FTIR software. For all spectra, the same wave-number positions were chosen. Each spectrum was acquired from 100 scans. For enhancing and further surveying peaks or specific shoulders, a Fourier Self-Deconvolution technique was used followed by spectral subtraction with sound healthy dentin set as reference.

FIG. 1a shows the resulting deconvoluted FTIR spectra. Curves A and B result from samples taken from the healthy dentin tissue of the two extracted teeth. Curves C and D result from samples taken from the inner layer of carious tissue of the two extracted teeth. Close inspection shows that curves C and D exhibit a small peak (a "shoulder") at 1740 $cm^{-1}$. This peak is lacking in curves A and B. The presence of a peak at 1740 $cm^{-1}$ in carious tissues has been reported earlier in WO 2008/048170, and has been attributed to the presence of ester groups in carious tissue.

Figure 1B:
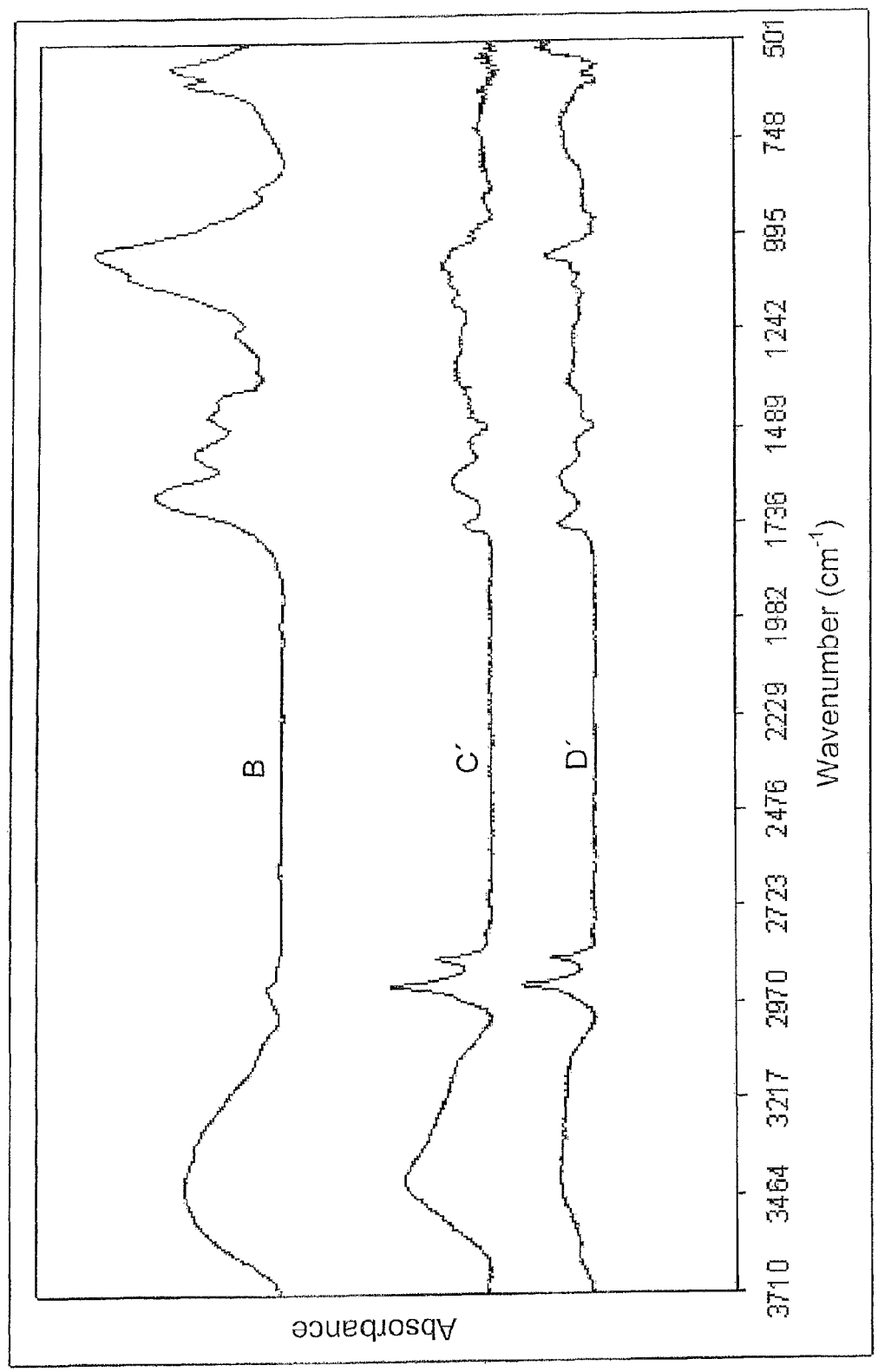
FIG. 1b shows FTIR spectra where curve B (healthy dentin tissue) has been subtracted from curve C and curve D in FIG. 1a resulting in curve C' and curve D'.

FIG. 1b shows an FTIR spectrum where curve B has been subtracted from curve C and curve D in FIG. 1a resulting in curve C' and curve D'. The peak at 1740 $cm^{-1}$ appears very clearly in curves C' and D'. This is clear evidence that ester groups are only present in carious dentin tissue and not in healthy dentin tissue.

Example 2

This experiment aimed to see if the added colours SEEK, Acid red 1, Lucifer Yellow, a combination of Lucifer Yellow and Acid red 1, or 5-(2-2-hydrazinyl-2-oxoethylthio)acetamido)-2-(3-hydroxy-6-oxo-6H-xanthen-9-yl)benzoic acid, Alexa Fluor® 594 and Alexa 350 bind to the surface of caries or not, after excavation down to a clinically caries free denoted surface. Experiments were performed during 4 days.

Whole caries infected tooth was added to an ortho acryl gel, which after hardening was used as a holder prior to sawing (saw of brand Zaw Micro Tone, German). Slices, having a thickness of 150 μm, were left over night in each colour to be tested (Day one). On the second day, the colours were washed out by rinsing the slices with MQ water and the teeth sections were photographed under either a microscope (6.7×; visible light), in UV (no microscope) or under a fluorescence microscope (100×). Thereafter, an aqueous salt solution (NaCl, 1 M) was added to the slices and incubated over night. On the third day the slices were washed with MQ water and thereafter the same detection procedures were used as described above. Finally the tooth slices were exposed to an aqueous solution of NaOH (0.5 M) over night. The washing and detection path were then repeated as described previously (Day 4).

Inspection of the slices after incubation with 1 M NaCl (Day 2) showed that the slice treated with Acid red 1 was discoloured and only little staining remained. After washing with NaOH (Day 4) no colouring of the slice treated with Acid red 1 could be detected using visible light and barely with microscope. In contrast, slices treated with Lucifer Yellow, a combination of Lucifer Yellow and Acid red 1,5-(2-2-hydrazinyl-2-oxoethylthio)acetamido)-2-(3-hydroxy-6-oxo-6H-xanthen-9-yl)benzoic acid, Alexa Fluor® 594 and Alexa 350 still contained colourants after day 4 as detected by fluorescence microscopy. Also, slices treated with SEEK remained stained though the colour seemed to be spread in the enamel, the healthy dentin and the root.

Figure 2A:
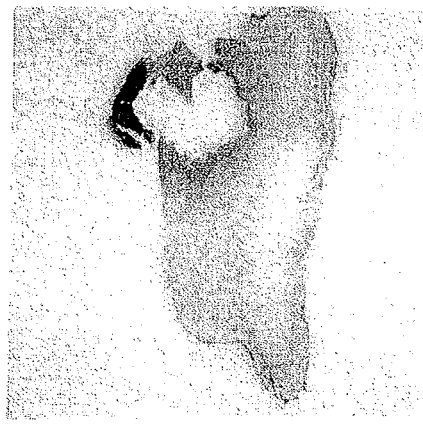
FIG. 2a shows staining of a tooth slice treated with 5-(2-2-hydrazinyl-2-oxoethylthio)acetamido)-2-(3-hydroxy-6-oxo-6H-xanthen-9-yl)benzoic acid after incubation with NaCl and NaOH.

FIG. 2a shows staining of a tooth slice treated with 5-(2-2-hydrazinyl-2-oxoethylthio)acetamido)-2-(3-hydroxy-6-oxo-6H-xanthen-9-yl)benzoic acid after incubation with NaCl and NaOH.

Figure 2B:
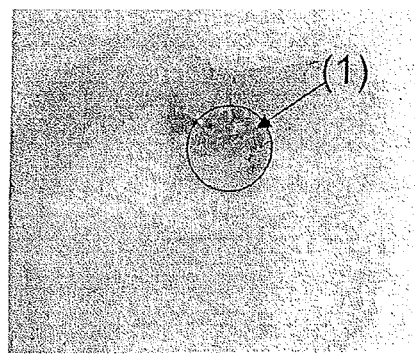
FIG. 2b shows staining of a tooth slice treated with Lucifer Yellow sodium salt after treatment with NaCl and NaOH. The stained area is indicated with a circle and (1).

FIG. 2b shows staining of a tooth slice treated with Lucifer Yellow sodium salt after treatment with NaCl and NaOH. The stained area is indicated with a circle and (1).

Figure 2C:
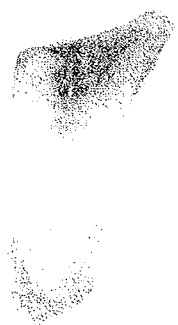
FIG. 2c shows staining of a tooth slice treated with Alexa Fluor 594® after treatment with NaCl and NaOH.

FIG. 2c shows staining of a tooth slice treated with Alexa Fluor 594® after treatment with NaCl and NaOH.

It was concluded that Acid red 1 binds in a reversible way to carious tissue in infected teeth, whereas 5-(2-2-hydrazinyl-2-oxoethylthio)acetamido)-2-(3-hydroxy-6-oxo-6H-xanthen-9-yl)benzoic acid, Lucifer Yellow, Alexa Fluor® and Alexa 350 bind irreversibly to carious dentin tissue in infected teeth. The reason why Acid red 1 binds reversibly may be that it is only capable of forming electrostatic bonds to carious tissue. SEEK binds in an unspecific way to carious tissue, healthy dentin and the root.

Example 3

Extracted permanent human teeth with no previous dental restorations were selected due to their severe carious tissue status and analysed with FTIR within one week after extraction. The outermost part of the carious dental lesions was removed. The remaining dental carious tissue was divided into two layers; one outer layer with discoloured, soft and infected dental carious tissue and one inner layer that was excavated down to the observed uncoloured hard surface of the remaining healthy dentin controlled by tactile procedures.

Healthy dentin tissue and carious dentin tissue from the innermost layer were collected. This healthy dentin tissue sample and carious dentin tissue sample were then each divided into three samples.

The healthy dentin tissue sample (26 mg) was divided and treated as follows. Sample one, hereinafter denominated S1, (11 mg) was repeatedly washed in purified water and put under vacuum and defined as untreated sample, i.e. the reference sample. The second sample, hereinafter denominated sample S2, (8 mg) was rigorously washed with purified water. Thereafter sample S2 was mixed with an aqueous solution of the hydrazine derivate Lucifer Yellow (13 mM) that after reaction overnight was washed with water and salt (NaCl, 1M). Fluorescence of bounded hydrazine derivate Lucifer Yellow was checked by a UV lamp. Next followed the addition of an aqueous solution of NaOH (0.5M), twice, to deprotonate the sample S2 and finally rinsed again with MQ water and dried over vacuum. The last step was used for determining whether or not the bonding was of electrostatic character. The third sample, hereinafter denominated sample S3, (7 mg) and the last procedure was treated with $NaBH_4$ (0.5 M in ethanol) and washed with concentrated ethanol to reduce aldehydes and ketones before the addition of an aqueous solution of the hydrazine derivate Lucifer Yellow (13 mM), repeated rinsing with purified water before dried and analysed.

The carious dentin tissue samples were treated in the same way as the healthy dentin sample above. The samples were denominated S4, S5 and S6. Sample S4 was subjected to the same treatment as sample S1 above. Sample S5 was subjected to the same treatment as sample S2 above. Sample S6 was subjected to the same treatment as sample S3 above.

Thus, in total 6 samples (three from the healthy dentin tissue and three from the carious dentin tissue) were analysed with FTIR within one week after extraction. The IR analyses were performed using a Nicolet 6700 FTIR spectrophotometer. A Smart Orbit diamond micro-AIR (Attenuated Total Reflectance) attachment was used to directly acquire spectra from the samples.

The instrument was purged with analytical instrument quality air to remove atmospheric $CO_2$ and $H_2O$, dried and purified with a Balstron type 75-60 conditioner.

The spectra were baseline corrected using the FTIR software. For all spectra, the same wavenumber positions were chosen. Each spectrum was acquired from 100 scans and the resolution was 4 $cm^{-1}$.

Figure 3A:
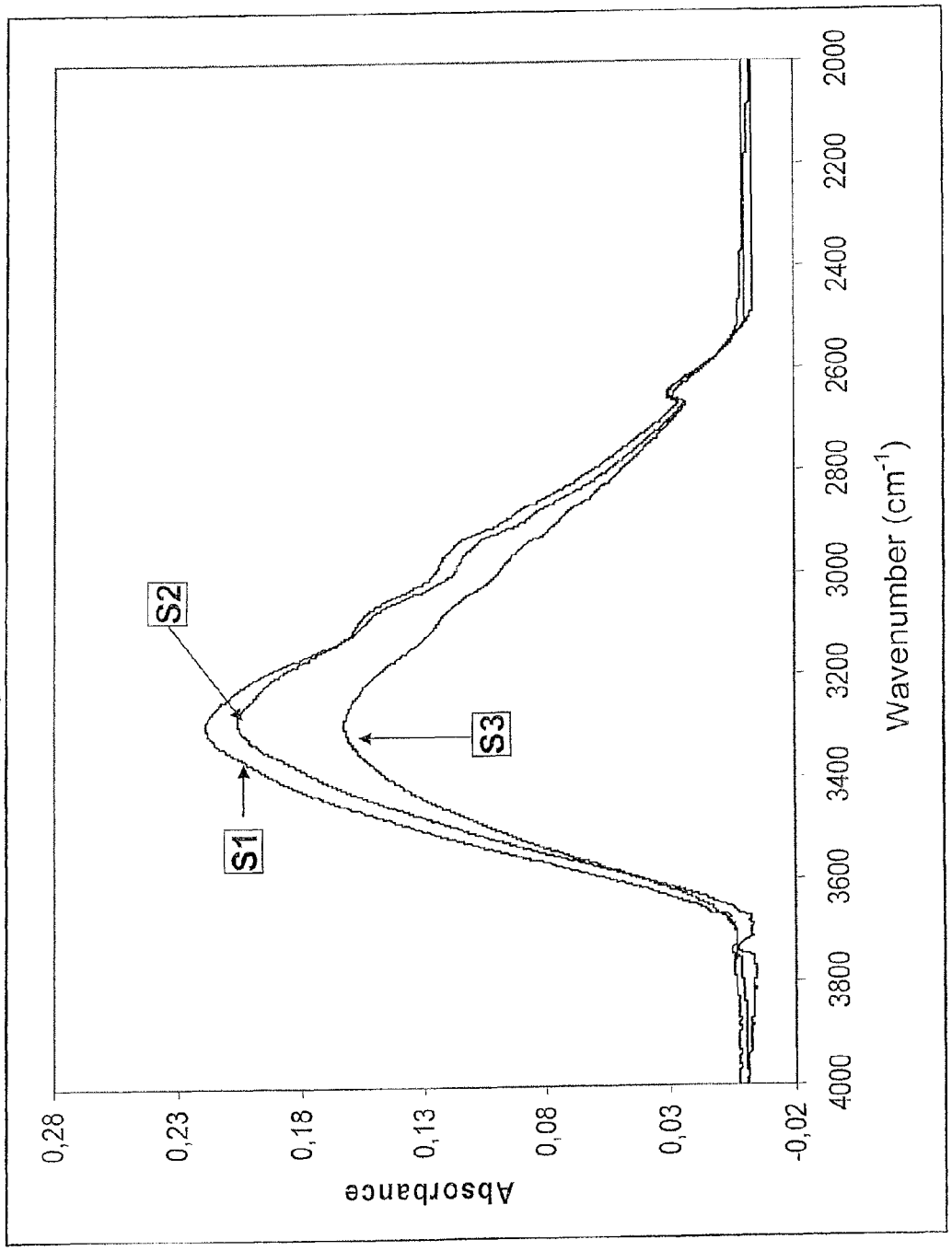
FIG. 3a shows the resulting FTIR spectra between 3700 and 2600 cm$^{-1}$ for healthy dentin tissue samples S1 (reference sample). S2 and S3 were treated with Lucifer Yellow.

FIG. 3a shows the resulting FTIR spectrum for samples S1, S2 and S3 between 3700 and 2600 $cm^{-1}$. The same peaks appeared for S1, S2 and S3.

Figure 3B:
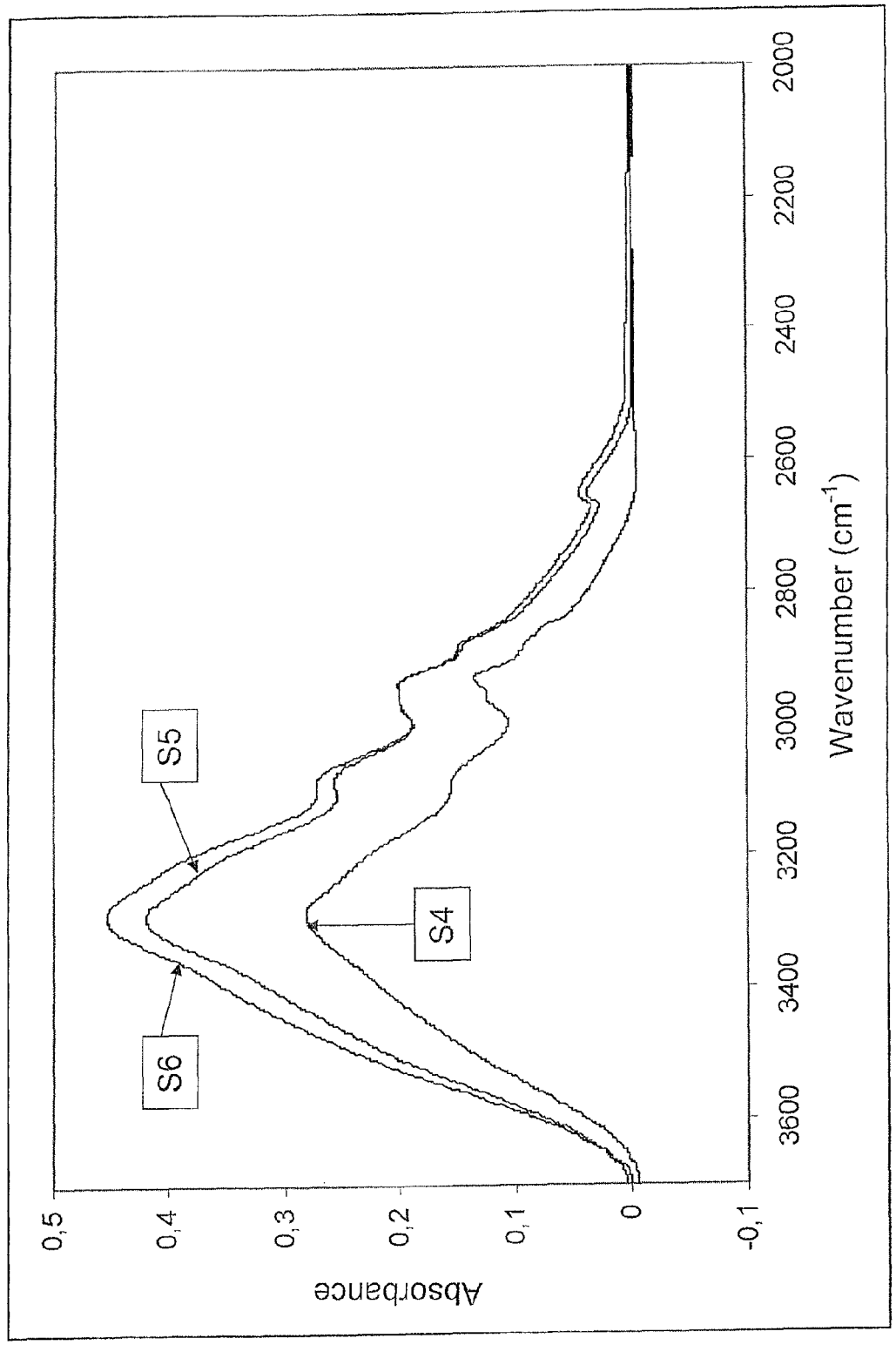
FIG. 3b shows the resulting FTIR spectra between 3700 and 2600 cm$^{-1}$ for carious dentin tissue samples S4 (reference sample). S5 and S6 were treated with Lucifer Yellow.

FIG. 3b shows the resulting FTIR spectrum for samples S4, S5 and S6 between 3700 and 2600 $cm^{-1}$. The same peaks appeared for S4, S5 and S6, different from the healthy dentin tissue samples in area of 2850 $cm^{-1}$.

Figure 3C:
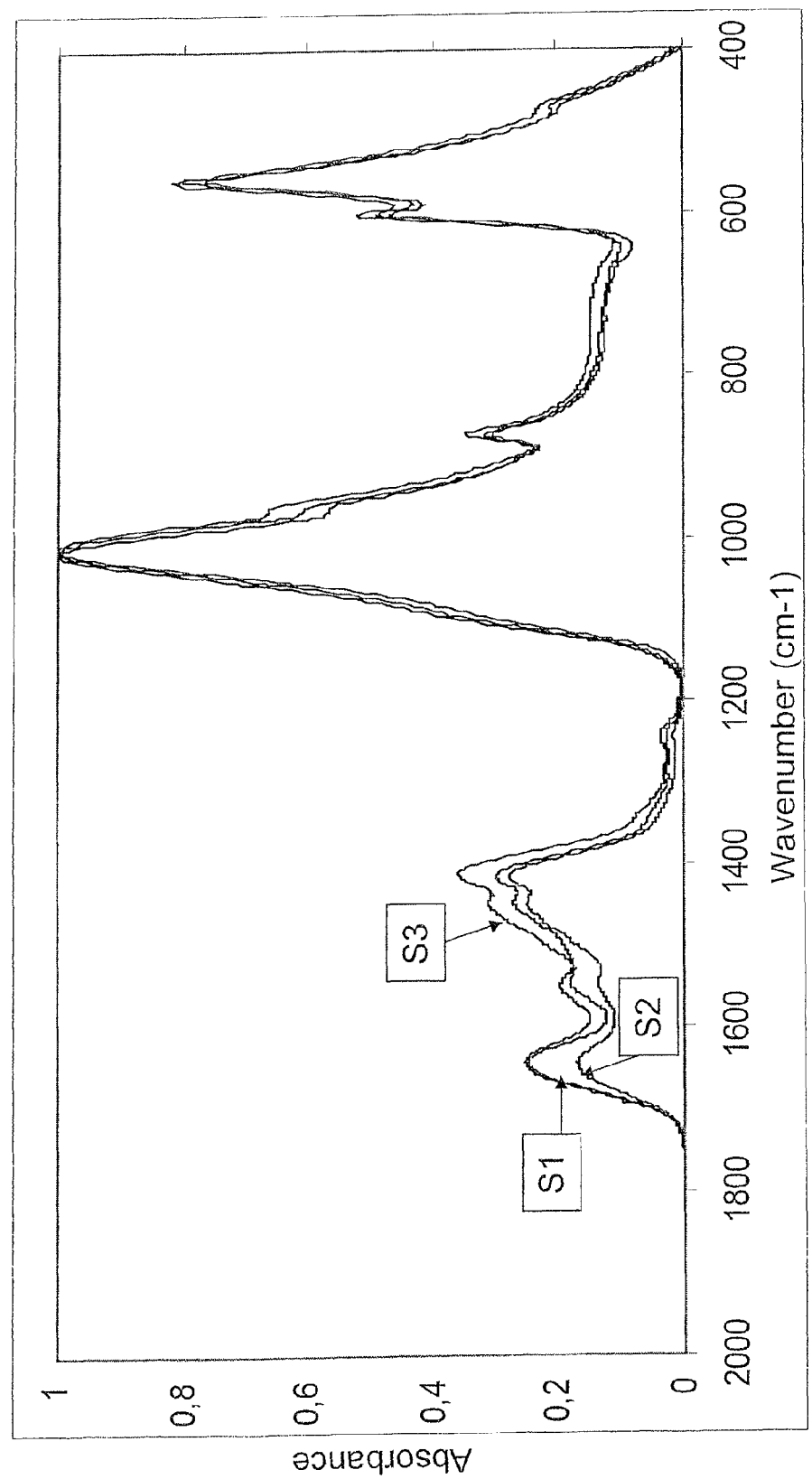
FIG. 3c shows the resulting FTIR spectra between 1800 and 400 cm$^{-1}$ for healthy dentin tissue samples S1 (reference sample). S2 and S3 were treated with Lucifer Yellow.

FIG. 3c shows the resulting FTIR spectrum for samples S1, S2 and S3 between 1800 and 400 $cm^{-1}$. The curves obtained from S1, S2 and S3 exhibited no peak at 1740 $cm^{-1}$.

Figure 3D:
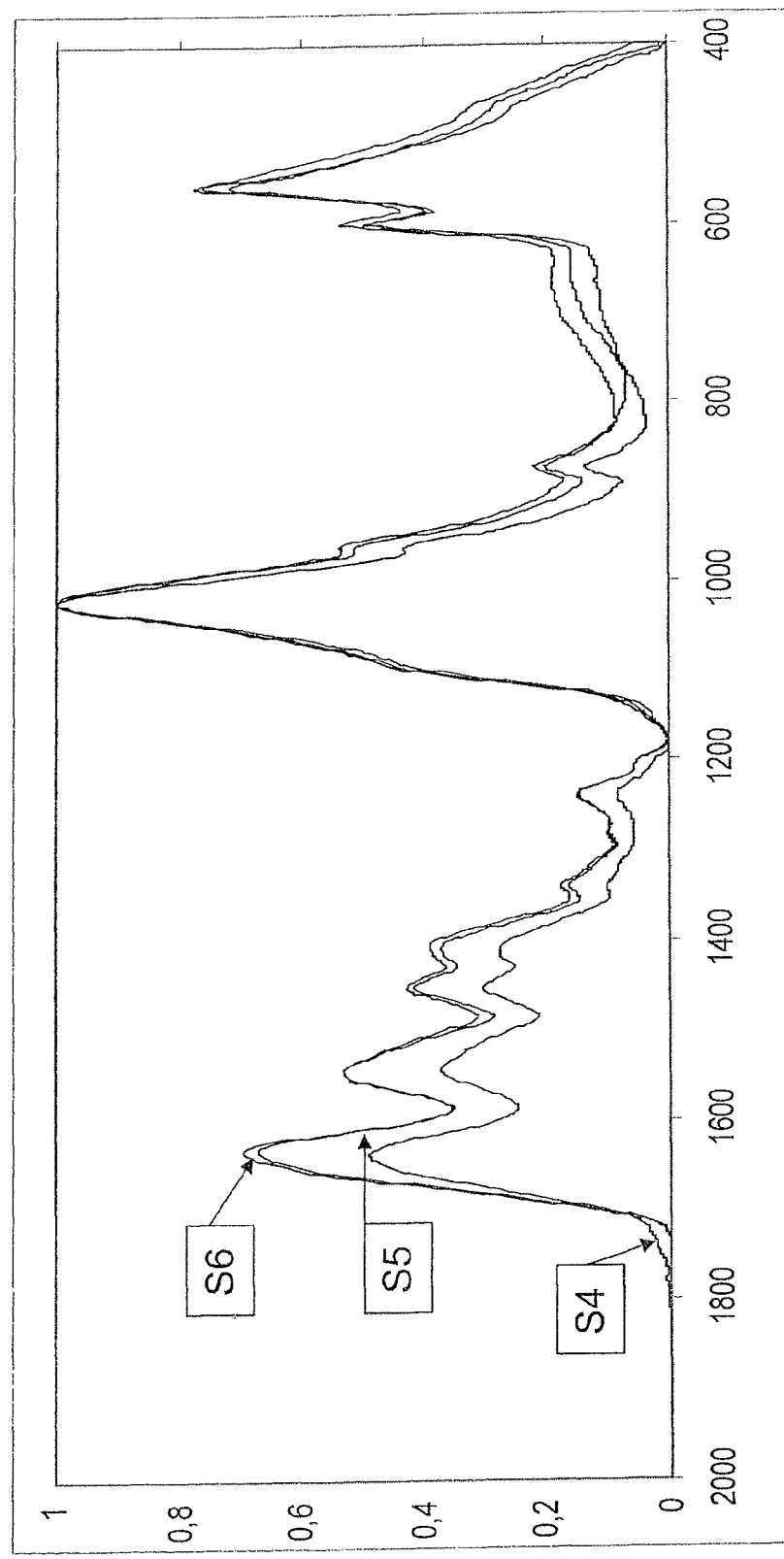
FIG. 3d shows the resulting FTIR spectra between 1800 and 400 cm$^{-1}$ for carious dentin tissue samples S4 (reference sample). S5 and S6 were treated with Lucifer Yellow.

FIG. 3d shows the resulting FTIR spectrum for samples S4, S5 and S6 between 1800 and 400 $cm^{-1}$. The curve obtained from S4 exhibited a peak at 1740 $cm^{-1}$. The curves obtained for S5 and S6 exhibited no peak at 1740 $cm^{-1}$.

Figure 3E:
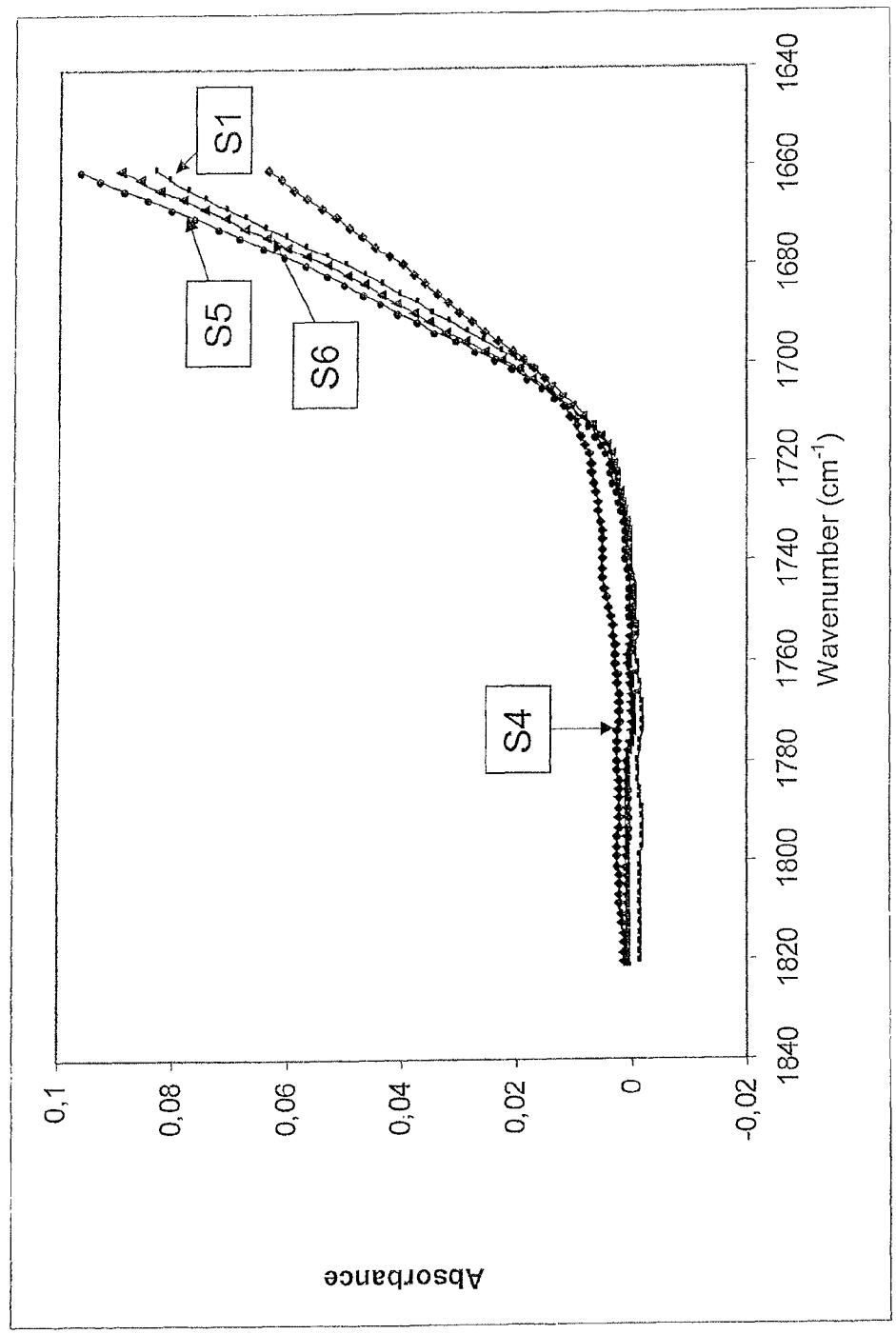
FIG. 3e shows the resulting FTIR spectra between 1800-1680 cm$^{-1}$ for carious dentin tissue samples S4 (ref), S5 and S6 were treated with Lucifer Yellow and compared with healthy dentin tissue S1 (reference sample).

FIG. 3e shows an enhanced region of the FTIR spectra for samples S4, S5, S6 and S1 (dentin ref) at wave numbers 1800-1680 $cm^{-1}$.

From FIGS. 3a and 3c it can be concluded that no reaction takes place between healthy dentin and the hydrazine derivative Lucifer Yellow. From FIG. 3d it can be concluded that reaction has taken place between the carious dentin tissue and the hydrazine derivative Lucifer Yellow, since the peak at 1740 $cm^{-1}$ is no longer present for samples S5 and S6. Accordingly, the hydrazine derivative Lucifer Yellow selectively reacts with carious dentin tissue.

Example 4

FTIR-ATR and TOF-SIMS analyses were performed on a sample group consisting of carious tissue inner most layers selected and estimated with an exactness of a working dentist. Samples were pooled from 4-6 teeth of inner layer of carious tissue (37 mg). The pooled sample was divided into two subgroups where one was exposed to the hydrazine derivate Lucifer Yellow and further analysed with TOF-SIMS and the other only analysed with FTIR-ATR. An aqueous solution of the hydrazine derivate Lucifer Yellow (1.8 mM) was added to the inner layer carious tissue (19 mg) and after 1 hour exposure washed with an aqueous solution of NaOH (0.5 M) and purified water before dried over vacuum. Events prolonged under a couple of hours from extraction to excavation to the drying and milling of the substances. Both FTIR-ATR and TOF-SIMS followed. FTIR-ATR was performed as described in Example 3 above. Time-of-flight secondary mass spectrometry is a sensitive surface analysis that gives information of the molecular composition of the surface down to ~1 nm in the material. The method is based on separations of charged secondary mass ions emitted from the sample surface after a pulsed beam of primary ions are projected to the sample holder. The primary ion used was 25 KeV $Bi^{3+}$ with beam (current) at 0.12 pA. Each sample was attached to double side tape and analysed with a TOF-SIMS instrument (TOF-SIMS IV, CAMECA/IONTOF, GmbH, Germany). Positive secondary ion mass spectra were recorded from different areas of the sample at a size of 200×200 $\mu m^+$ and separated in a mass analyser and next compared with known mass spectra from the Ion Spec application (IonTof, GmbH, Germany, ver. 4.1) linked with the TOF-SIMS instrument. Negative secondary ion mass spectra were also recorded but gave no further information.

Data acquisition time for each secondary ion spectra spectrum was 100 s.

Figure 4A:
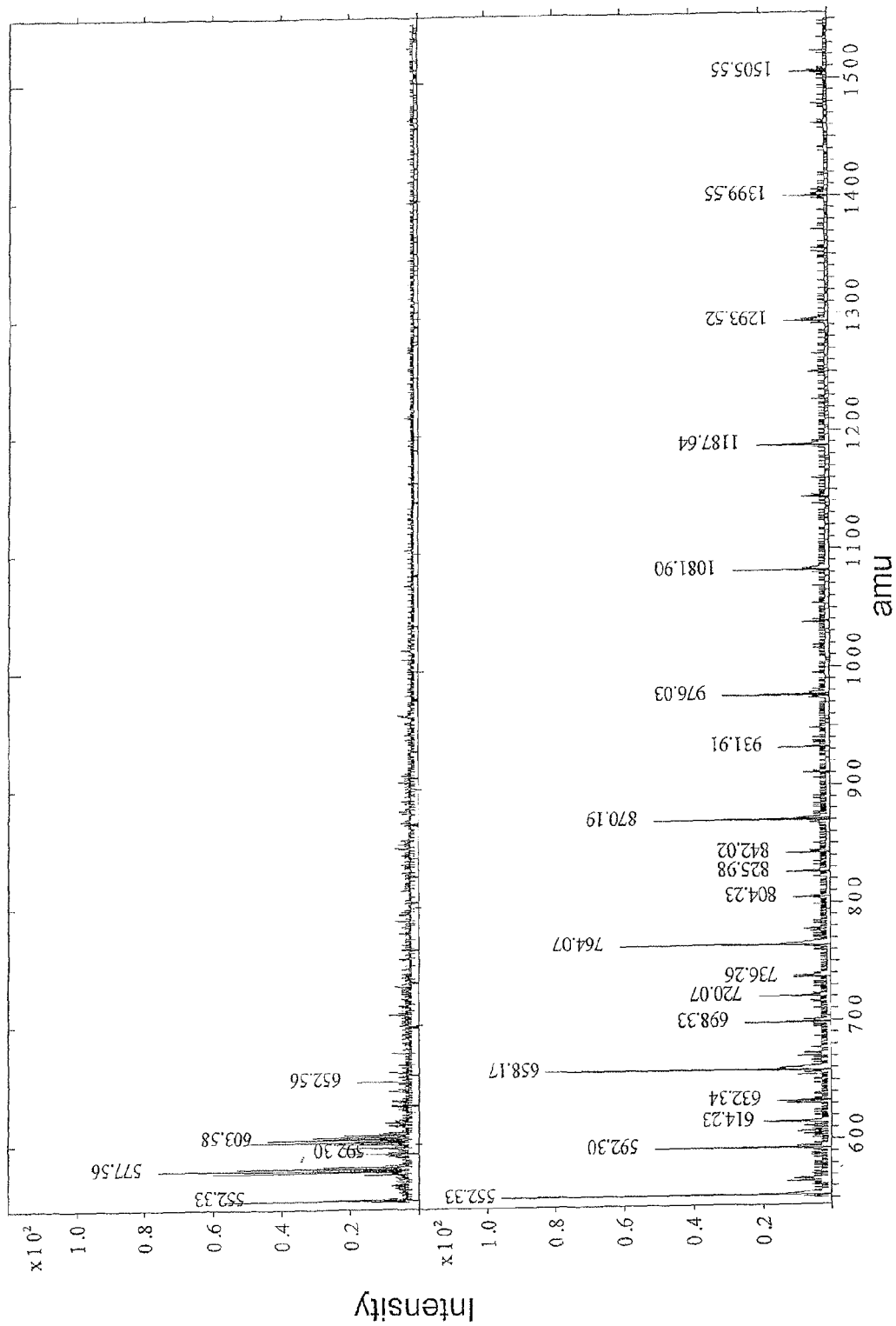
FIG. 4a shows positive TOF-SIMS spectra for carious dentin tissue. The upper spectrum shows carious dentin tissue. The lower spectrum shows carious dentin tissue treated with the hydrazine derivative Lucifer Yellow.

FIG. 4a shows positive TOF-SIMS spectra for carious dentin tissue. The upper spectrum was recorded for the sample of carious dentin tissue that had been milled but not subjected to treatment with hydrazine (i.e. the carious dentin tissue reference). The lower spectrum was recorded for the sample of carious dentin tissue that had been treated with the hydrazine derivative Lucifer Yellow.

Figure 4B:
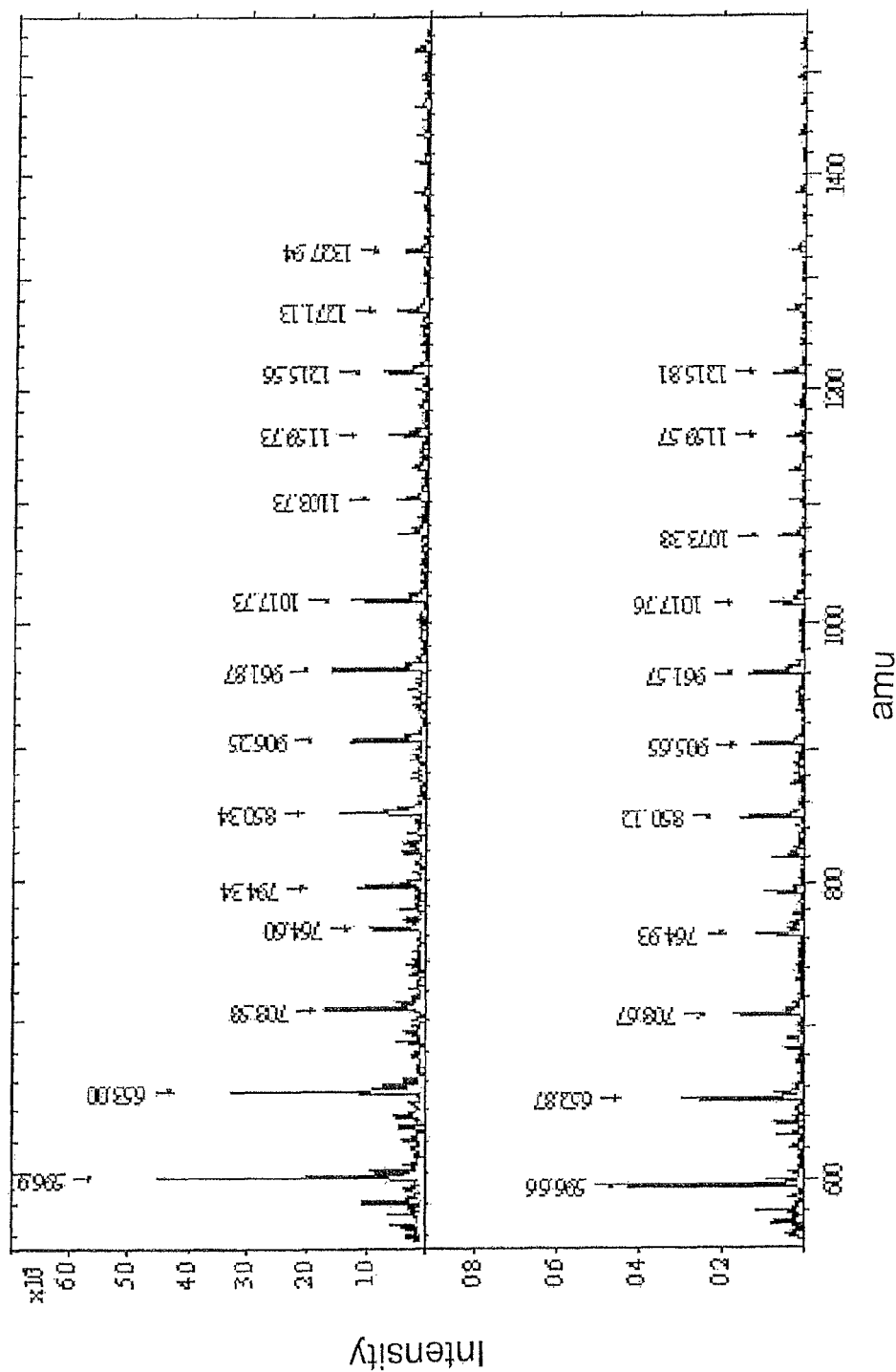
FIG. 4b shows positive TOF-SIMS spectra for healthy dentin tissue. The upper spectrum shows healthy dentin tissue. The lower spectrum shows healthy dentin tissue treated with the hydrazine derivative Lucifer Yellow.

FIG. 4b shows positive TOF-SIMS spectra for healthy dentin tissue. The upper spectrum was recorded for the sample of healthy dentin tissue that had been milled but not subjected to treatment with hydrazine (i.e. the healthy dentin tissue reference). The lower spectrum was recorded for the sample of healthy dentin tissue that had been treated with the hydrazine derivative Lucifer Yellow.

These spectra show that the carious dentin tissue reference holds the largest mass at 652.56 u, whereas the carious dentin tissue that had been treated with hydrazine Lucifer Yellow holds masses up to 1505.56 u. Lucifer Yellow has no masses higher than 600 u (not shown). It can therefore be concluded that masses higher than that seen for the carious dentin tissue reference sample at 652.56 u (FIG. 4a, upper spectrum) originate from a structure of carious dentin tissue covalently bonded to the hydrazine derivate Lucifer Yellow (FIG. 4a lower spectrum). The observed pattern of mass units repeatedly differing by 106 mass units corresponding to $C5NO2$ may be ascribed to Lucifer Yellow covalently bound to the carious tissue. This pattern was not detected for the healthy dentin samples. The positive mass spectra of the healthy dentin samples treated with Lucifer Yellow (FIG. 4b, lower spectrum) were similar to the positive mass spectra of untreated healthy dentin sample (FIG. 4b, upper spectrum). Both hold repeated masses with a difference of 56 mass units, that correlates with CaO of the mineral. It was therefore concluded that Lucifer Yellow did not react with healthy dentin. Accordingly, the hydrazine derivative Lucifer Yellow selectively reacts with carious dentin tissue.

Example 5

Carious dentin tissue of a pre molar tooth was treated with Carisolv® to obtain a cavity and subsequently stained with an aqueous solution of the hydrazine derivative Alexa 594.

The concentration of the aqueous solution of the hydrazine derivative Alexa 594 was 15-50 mM. As a result, the cavity exhibited an intense dark bluish colour. Carisolv® was added to the cavity and excavation took place with a hand instrument from Mediteam Dental AB to reach a carious free level. Rinsing with MQ water was performed and a photograph was taken that showed a surface that appeared to be free of caries. A dentist performed tactile control of this surface and confirmed that the surface was free of caries. In order to be absolutely certain that no caries remained further staining of the surface with Alexa 594 was attempted resulting in a very slight staining at the center of the cavity. The slightly stained surface was subjected to treatment with Carisolv® followed by excavation with a hand instrument. A final attempt to stain the thus obtained surface was made with Alexa 594, but no staining took place. It was therefore concluded that all carious dentin tissue of the tooth had been removed. It was concluded that a hydrazine derivative such as Alexa 594 can be used in combination with a chemical means for carious dentin tissue such as Carisolv® for selective detection and removal of carious dentin tissue. Further, it was concluded that staining with Alexa 594 is a better and more sensitive method for detecting carious dentin tissue than tactile control performed by a dentist.

Example 6

Carious dentin tissue of a pre molar tooth stained with an aqueous solution of the hydrazine derivative Alexa 594 in a concentration of 15-50 mM was subjected to mechanical treatment by a dentist's drill until no staining could be visually detected. An aqueous solution of the hydrazine derivative Alexa 594 in a concentration of 15-50 mM was added and resulted in staining. The stained surface was subjected to drilling until no staining could be visually detected. A dentist examined the surface visually and with a tactile instrument and concluded that the surface was free of caries. Surprisingly, addition of an aqueous solution of the hydrazine derivative Alexa 594 in a concentration of 15-50 mM to the surface free of caries resulted in staining. Again, drilling of the stained surface took place until no staining could be observed. Addition of an aqueous solution of the hydrazine derivative Alexa 594 in a concentration of 15-50 mM took place, and resulted in staining. Drilling and staining as described above in this example was repeated several times. The result was that staining always took place after the drilling had been performed. It was concluded that selective detection and removal of carious dentin tissue using a hydrazine derivative in combination with a dentist's drill was not possible. It is suggested that the unsuccessful attempt to selectively detect and remove carious dentin tissue may be due to the formation of a smear layer. This is in contrast to the successful selective detection and removal of carious dentin tissue using a hydrazine derivative in combination with a chemical means for treatment of carious dentin tissue as described in Example 5.

The invention claimed is:
1. A kit of parts for detection and removal of carious dentin tissue comprising:
(i) one or more compounds of a hydrazine derivative of formula (I)

RNHNH$_2$ (I)

wherein R is a chemical group containing a chromophore, wherein the hydrazine derivative of formula (I) irreversibly labels carious dentin tissue and selectively labels carious dentin tissue without labelling healthy dentin tissue, and (ii) means for chemical treatment of carious dentin tissue being able to soften and/or dissolve carious dentin tissue, wherein the means for chemical treatment comprises a preparation containing an active, caries-dissolving two-component liquid in the form of a first active, caries-dissolving component and a second component that reduces the aggressiveness of the active component to mucous membranes, and a viscosity increasing substance.

2. A kit of parts according to claim 1, wherein the one or more compounds of the hydrazine derivative is selected from the group consisting of:

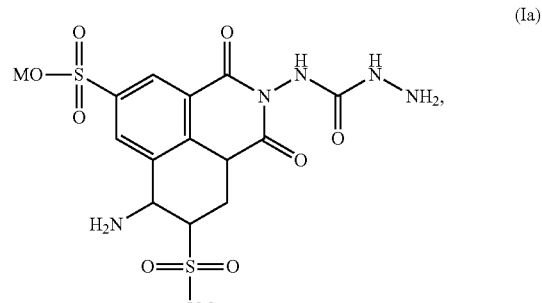

(Ia)

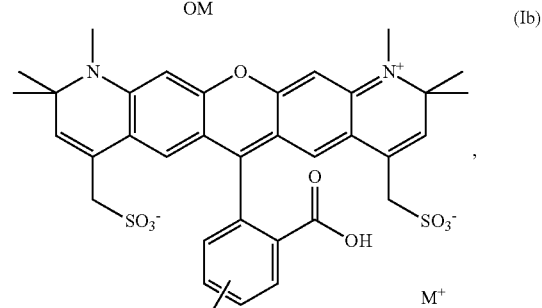

(Ib)

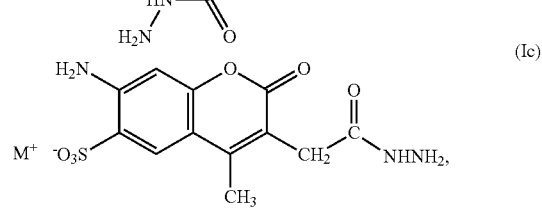

(Ic)

wherein M or M$^+$ represents a monovalent metal ion selected from the group consisting of Li$^+$, K$^+$, and Na$^+$, and

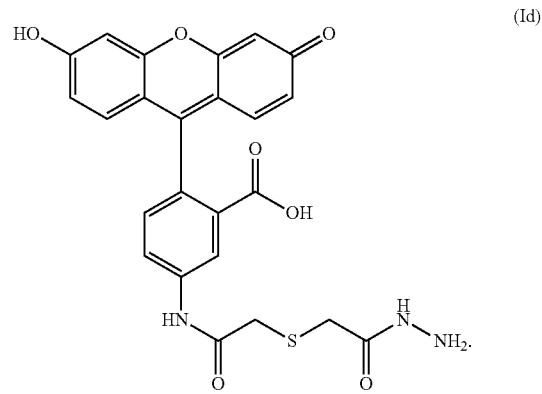 [SMILES: NNC(=O)CSCC(=O)Nc1ccc(-c2c3ccc(=O)cc-3oc3cc(O)ccc23)c(C(=O)O)c1]

(Id)

3. A kit of parts according to claim 1, wherein the kit of parts further comprises a device for mechanical removal of the carious dentin tissue that has been softened and/or dissolved by the means for chemical treatment of carious dentin tissue.

4. A kit of parts according to claim 1, wherein the active caries-dissolving component is $Cl^{1+}$, potassium hypochlorite, or sodium hypochlorite.

5. A kit of parts according to claim 1, wherein the component which reduces the aggressiveness of the active component to mucous membranes comprises amino acids or a mixture of aminoethanediol, 1-amino-3,3-dimethylpropanol and 1,5-diaminopentanol.

6. A kit of parts according to claim 5, wherein the amino acids are three amino acids with different charge states: one neutral, one with a negative net charge, and one with a positive net charge.

7. A kit of parts according to claim 1, wherein the viscosity increasing substance is a gel.

8. A kit of parts according to claim 7, wherein the gel is carboxymethyl cellulose or a polysaccharide substance.

9. A kit of parts according to claim 1, wherein the preparation is an aqueous composition comprising a first active component NaOCl in a concentration of 1-2% (w/w), a second component having a pH between 9.5 and 10.5 and comprising a mixture of glutamic acid, leucine, and lysine 0.5-1.5% (w/w), NaCl 0.5% (w/w), and high viscosity carboxymethyl cellulose gel 2.5-5% (w/w).

10. A kit of parts according to claim 1, wherein the preparation is an aqueous composition comprising a first active component NaOCl in a concentration of 1-2% (w/w), a second component having a pH between 9.5 and 10.5 and comprising a mixture of glutamic acid, leucine, and lysine 0.5-1.5% (w/w), NaCl 0.5% (w/w), $TiO_2$ 0.03% (w/w), and medium viscosity carboxymethyl cellulose gel 2.5-5% (w/w).

11. A composition comprising an active, caries-dissolving two-component liquid in the form of a first active, caries-dissolving component and a second component which reduces the aggressiveness of the active component to mucous membranes, a viscosity increasing substance, and one or more compounds of a hydrazine derivative of formula (I)

$$RNHNH_2 \qquad (I)$$

wherein R is a chemical group containing a chromophore, wherein the hydrazine derivative of formula (I) irreversibly labels carious dentin tissue and selectively labels carious dentin tissue without labelling healthy dentin tissue.

12. A composition according to claim 11, wherein the one or more compounds of the hydrazine derivative is selected from the group consisting of:

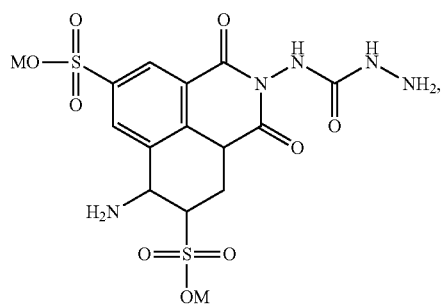

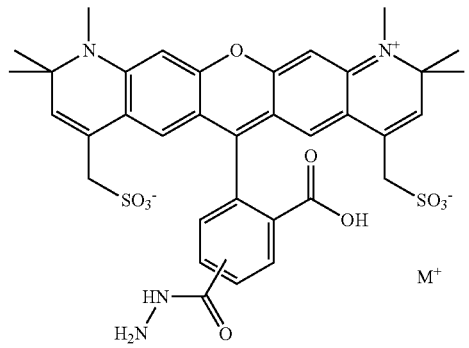

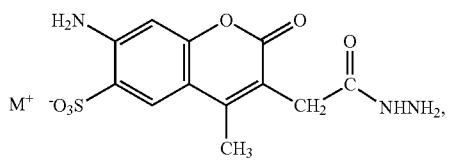

wherein M or $M^+$ represents a monovalent metal ion selected from the group consisting of $Li^+$, $K^+$, and $Na^+$, and

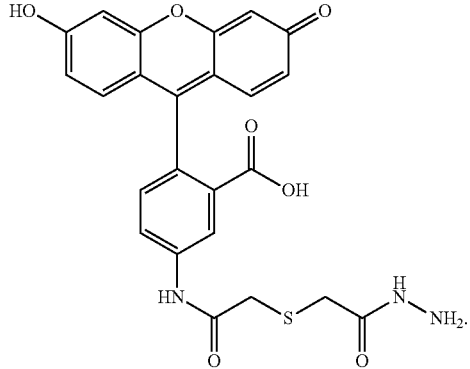

13. A composition according to claim 11, wherein the first active component comprises NaOCl in a concentration of 1-2% (w/w), wherein the second component has a pH between 9.5 and 10.5 and comprises a mixture of glutamic acid, leucine, and lysine in a concentration of 0.5-1.5% (w/w), and NaCl in a concentration of 0.5% (w/w), and wherein the viscosity increasing substance comprises a high viscosity carboxymethyl cellulose gel in a concentration of 2.5-5% (w/w).

14. A composition according to claim 11, wherein the first active component comprises NaOCl in a concentration of 1-2% (w/w), wherein the second component has a pH between 9.5 and 10.5 and comprises a mixture of glutamic acid, leucine, and lysine in a concentration of 0.5-1.5% (w/w), NaCl in a concentration of 0.5% (w/w), and $TiO_2$ in a concentration of 0.03% (w/w), and wherein the viscosity increasing substance comprises a medium viscosity carboxymethyl cellulose gel in a concentration of 2.5-5% (w/w).

15. A method for irreversibly and selectively labelling and removing carious dentin tissue comprising the steps of:
    irreversibly labelling carious dentin tissue and selectively labelling carious dentin tissue without labelling healthy dentin tissue by applying the composition of claim 11 to one or more teeth comprising carious dentin tissue or the root canal of a tooth comprising carious dentin tissue and healthy dentin tissue; and (ii) removing the labelled carious dentin tissue mechanically.

16. A method according to claim 15, wherein the one or more compounds of the hydrazine derivative is selected from the group consisting of:

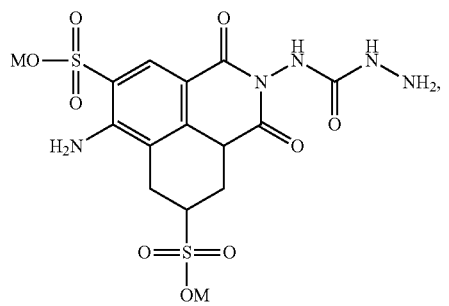
(Ia)

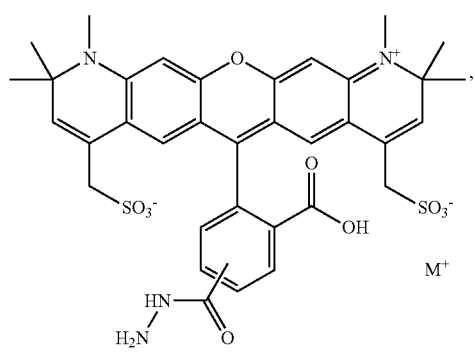
(Ib)

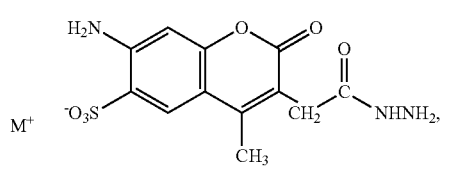
(Ic)

wherein M or $M^+$ represents a monovalent metal ion selected from the group consisting of $Li^+$, $K^+$, and $Na^+$, and

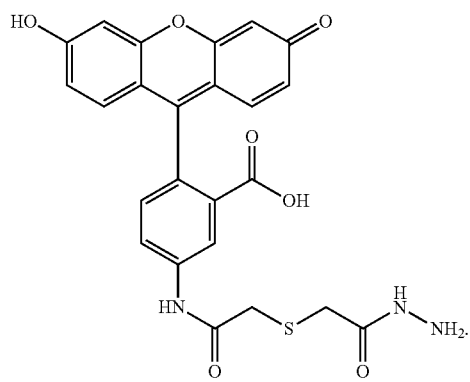
(Id)

17. A method according to claim 15, wherein the composition is applied to one or more teeth comprising carious dentin tissue and healthy dentin tissue.

18. A method for irreversibly and selectively labelling and removing carious dentin tissue comprising the steps of:

(i) irreversibly labelling carious dentin tissue and selectively labelling carious dentin tissue without labelling healthy dentin tissue by applying one or more compounds of a hydrazine derivative of formula (I)

$$RNHNH_2 \quad (I)$$

wherein R is a chemical group containing a chromophore, onto one or more teeth comprising carious dentin tissue and healthy dentin tissue or the root canal of a tooth comprising carious dentin tissue and healthy dentin tissue, wherein the hydrazine derivative of formula (I) irreversibly labels carious dentin tissue and selectively labels carious dentin tissue without labelling healthy dentin tissue, (ii) applying means for chemical treatment of carious dentin tissue to the labelled carious tissue, wherein the means for chemical treatment comprises a preparation containing an active, caries-dissolving two-component liquid in the form of a first active, caries-dissolving component and a second component that reduces the aggressiveness of the active component to mucous membranes, and a viscosity increasing substance, and (iii) removing the labelled carious dentin tissue mechanically.

19. A method according to claim 18, wherein the one or more compounds of the hydrazine derivative is selected from the group consisting of:

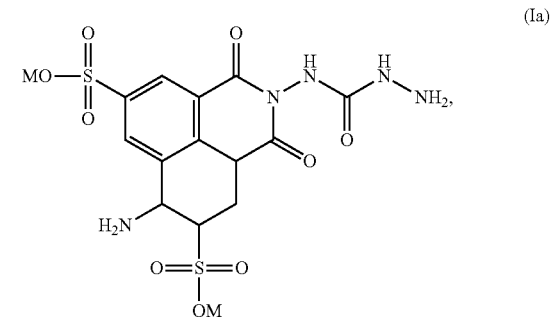
(Ia)

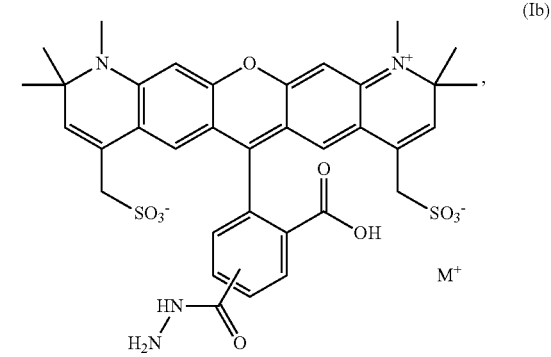
(Ib)

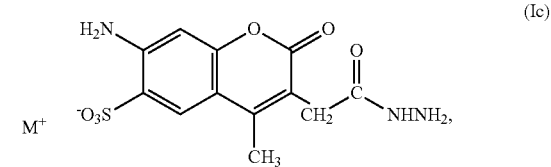
(Ic)

wherein M or M⁺ represents a monovalent metal ion selected from the group consisting of $Li^+$, $K^+$, and $Na^+$, and

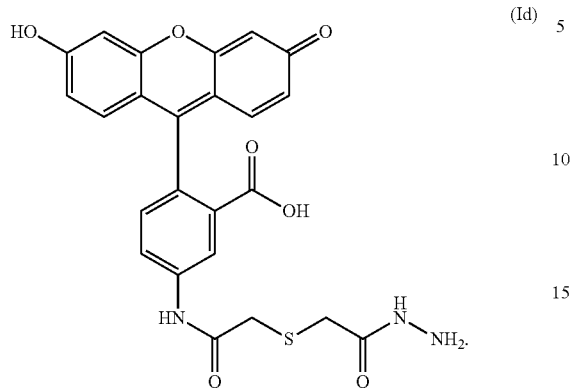

(Id)

20. A method according to claim 18, wherein the means for chemical treatment comprises a preparation comprising an active, caries-dissolving two-component liquid in the form of a first active, caries-dissolving component and a second component which reduces the aggressiveness of the active component to mucous membranes, and a viscosity increasing substance.

21. A method according to claim 18, wherein the hydrazine derivative is applied to one or more teeth comprising carious dentin tissue and healthy dentin tissue.

* * * * *